(12) United States Patent
Orme et al.

(10) Patent No.: US 7,034,027 B2
(45) Date of Patent: Apr. 25, 2006

(54) FUSED HETEROCYCLIC DERIVATIVES AS PHOSPHODIESTERASE INHIBITORS

(75) Inventors: Mark W. Orme, Seattle, WA (US); Jason Scott Sawyer, Indianapolis, IN (US); Lisa M. Schultze, Woodinville, WA (US)

(73) Assignee: Lilly Icos LLC, Wilmington, DE (US)

( * ) Notice: Subject to any disclaimer, the term of this patent is extended or adjusted under 35 U.S.C. 154(b) by 139 days.

(21) Appl. No.: 10/333,146

(22) PCT Filed: Jul. 9, 2001

(86) PCT No.: PCT/US01/21678

§ 371 (c)(1),
(2), (4) Date: Jan. 15, 2003

(87) PCT Pub. No.: WO02/10166

PCT Pub. Date: Feb. 7, 2002

(65) Prior Publication Data

US 2003/0207867 A1 Nov. 6, 2003

Related U.S. Application Data

(60) Provisional application No. 60/222,451, filed on Aug. 2, 2000.

(51) Int. Cl.
| | | |
|---|---|---|
| *C07D 471/14* | (2006.01) | |
| *C07D 487/14* | (2006.01) | |
| *A61K 31/4985* | (2006.01) | |
| *A61P 9/12* | (2006.01) | |
| *A61P 15/10* | (2006.01) | |

(52) U.S. Cl. ........................ 514/250; 544/343
(58) Field of Classification Search ............... 544/343; 514/250
See application file for complete search history.

(56) References Cited

U.S. PATENT DOCUMENTS

| | | | | |
|---|---|---|---|---|
| 5,859,006 A | * | 1/1999 | Daugan | 514/249 |
| 5,981,527 A | * | 11/1999 | Daugan et al. | 514/250 |
| 6,046,199 A | | 4/2000 | Pamukcu et al. | |
| 6,140,329 A | * | 10/2000 | Daugan | 514/250 |

FOREIGN PATENT DOCUMENTS

| | | |
|---|---|---|
| EP | 1 022 026 | 7/2000 |
| WO | WO 95/19978 | 7/1995 |
| WO | WO 97/03675 | 2/1997 |
| WO | WO 97/03985 | 2/1997 |
| WO | WO 9703675 A1 * | 2/1997 |
| WO | WO 00/66099 | 11/2000 |
| WO | WO 00/66114 | 11/2000 |

OTHER PUBLICATIONS

Wang et al., Organic Letters vol. 1 (10) 1647-1649, 1999.*
Lucas et al. Pharmacological Reviews 52 (3), 375-413, 2000.*
West, Anthony R., Solid State Chemistry and its Applications, Wiley, New York, 1988, pp. 358 & 365.*
Loevezijn et al. Tetrahedron Letters 39: 4737-4740, 1998.*
E. Sybertz et al., *Exp. Opin. Ther. Patents*, 7(6): 631-639 (1997).

* cited by examiner

*Primary Examiner*—Venkataraman Balasubramanian
(74) *Attorney, Agent, or Firm*—Marshall, Gerstein & Borun LLP

(57) ABSTRACT

Compounds of general structural formula (I) and use of the compounds and salts and solvates thereof, as therapeutic agents.

21 Claims, No Drawings

FUSED HETEROCYCLIC DERIVATIVES AS PHOSPHODIESTERASE INHIBITORS

CROSS REFERENCE TO RELATED APPLICATION

This is the U.S. national phase application of International Application No. PCT/US01/21678, filed Jul. 9, 2001, which claims the benefit of U.S. provisional patent application Ser. No. 60/222,451, filed Aug. 2, 2000.

This invention relates to a series of compounds, to methods of preparing the compounds, to pharmaceutical compositions containing the compounds, and to their use as therapeutic agents. In particular, the invention relates to compounds that are potent and selective inhibitors of cyclic guanosine 3',5'-monophosphate specific phosphodiesterase (cGMP-specific PDE), in particular PDE5, and have utility in a variety of therapeutic areas wherein such inhibition is considered beneficial, including the treatment of cardiovascular disorders and erectile dysfunction.

SUMMARY OF THE INVENTION

The present invention provides compounds of formula (I)

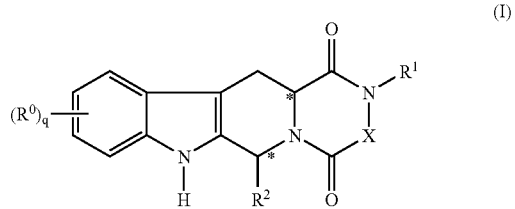

(I)

wherein $R^0$, independently, is selected from the group consisting of halo and $C_{1-6}$alkyl;

$R^1$ is selected from the group consisting of hydrogen, $C_{1-6}$alkyl, $C_{2-6}$alkenyl, $C_{2-6}$alkynyl, halo$C_{1-6}$-alkyl, $C_{3-8}$cycloalkyl, $C_{3-8}$cycloalkyl$C_{1-3}$alkyl, aryl$C_{1-3}$-alkyl, and heteroaryl$C_{1-3}$alkyl;

$R^2$ is selected from the group consisting of an optionally substituted monocyclic aromatic ring selected from the group consisting of benzene, thiophene, furan, and pyridine, and an optionally substituted bicyclic ring

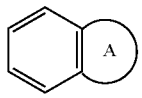

wherein the fused ring A is a 5- or 6-membered ring, saturated or partially or fully unsaturated, and comprises carbon atoms and optionally one or two heteroatoms selected from oxygen, sulfur, and nitrogen;

X is selected from the group consisting of $NR^a$, O, S, $CR^3R^4$, $CH_2CR^3R^5$, and $CR^3R^5CH_2$;

$R^3$ is selected from the group consisting of hydrogen and $C_{1-3}$alkyl;

or $R^1$ and $R^3$ together represent a 3- or 4-membered alkyl or alkenyl chain component of a 5- or 6-membered ring;

or $NR^a$, $R^1$, and the nitrogen to which $R^1$ is attached, form a 5- or 6-membered heterocyclic ring;

$R^4$ is selected from the group consisting of $C_{1-6}$alkyl, halo$C_{1-4}$alkyl, aryl, heteroaryl, Het, $C_{3-8}$-cycloalkyl, $OR^a$, $C(=O)OR^a$, $C(=O)R^a$, $C(=O)NR^aSO_2R^b$, $C(=O)NR^aR^b$, $C(=S)NR^aR^b$, $C_{1-6}$alkyleneC(=O)$OR^a$, $C_{1-4}$alkyl-eneC(=O)$NR^aR^b$, $C_{1-4}$alkyleneNR$^aR^b$, $C_{1-4}$alkyleneOR$^a$, $C_{1-4}$alkyleneSO$_2NR^aR^b$, $C_{1-4}$alkylenearyl, $C_{1-4}$alkyleneheteroaryl, $C_{1-4}$alkyleneHet, $C_{1-4}$alkyleneC(=O)$C_{1-4}$alkyleneHet, $C_{1-4}$alkyleneC(=O)Het, $C_{1-4}$alkyleneC(=O)$OR^a$, C(=O)—$C_{1-4}$alkyleneHet, C(=O)NR$^a$alkyleneOR$^b$, C(=O)NR$^aC_{1-4}$alkyleneHet, NR$^aC_{1-4}$alkyleneNR$^aR^b$, NR$^aC(=O)R^b$, NR$^aC(=O)NR^aR^b$, N(SO$_2C_{1-4}$alkyl)$_2$, and NR$^a$(SO$_2C_{1-4}$alkyl), with the proviso that when $R^3$ is hydrogen, $R^4$ is different from $C_{1-3}$alkyl;

or $R^1$ and $R^4$ together represent a 3- or 4-membered carbocyclic or heterocyclic chain component, either saturated or unsaturated, of a 5- or 6-membered ring;

or $R^3$ and $R^4$ together represent a 4- to 6-membered alkyl or alkenyl chain component of a 5- to 7-membered ring;

$R^5$ is selected from the group consisting of hydrogen, $C_{1-6}$alkyl, halo$C_{1-4}$alkyl, aryl, heteroaryl, Het, $C_{3-8}$cycloalkyl, $OR^a$, $C(=O)OR^a$, $C(=O)R^a$, $C(=O)$—$NR^aSO_2R^b$, $C(=O)NR^aR^b$, $C(=S)NR^aR^b$, $C_{1-6}$alkyleneC(=O)$OR^a$, $C_{1-4}$alkyleneC(=O)$NR^aR^b$, $C_{1-4}$alkyleneNR$^aR^b$, $C_{1-4}$alkyleneOR$^a$, $C_{1-4}$alkyleneSO$_2NR^aR^b$, $C_{1-4}$alkylenearyl, $C_{1-4}$alkyleneheteroaryl, $C_{1-4}$alkyleneHet, $C_{1-4}$alkyleneC(=O)$C_{1-4}$-alkyleneHet, $C_{1-4}$alkyleneC(=O)Het, $C_{1-4}$alkyleneC(=O)—$OR^a$, $C(=O)C_{1-4}$alkyleneHet, C(=O)NR$^a$alkyleneOR$^b$, C(=O)—NR$^aC_{1-4}$alkyleneHet, NR$^aC_{1-4}$alkyleneNR$^aR^b$, NR$^aC(=O)R^b$, NR$^aC(=O)NR^aR^b$, N(SO$_2C_{1-4}$alkyl)$_2$, and NR$^a$(SO$_2C_{1-4}$alkyl);

$R^a$ and $R^b$, independently, are selected from the group consisting of hydrogen, $C_{1-8}$alkyl, aryl, heteroaryl, halo$C_{1-6}$alkyl, $C_{1-4}$alkyleneHet, aryl$C_{1-3}$-alkyl, heteroaryl$C_{1-3}$alkyl, $C_{1-4}$alkylenearyl, $C_{3-8}$-cycloalkyl, $C_{1-3}$alkyleneheteroaryl, and Het;

Het is a 4- to 7-membered heterocyclic group, saturated or partially unsaturated, containing at least one heteroatom selected from the group consisting of oxygen, nitrogen, and sulfur, and optionally substituted with one or more of $C_{1-4}$alkyl, NR$^aR^b$, and C(=O)$OR^a$;

q is 0, 1, 2, 3, or 4; and pharmaceutically acceptable salts and solvates (e.g., hydrates) thereof.

As used herein, the term "alkyl" includes straight chained and branched hydrocarbon groups containing the indicated number of carbon atoms, typically methyl, ethyl, and straight chain and branched propyl and butyl groups. The hydrocarbon group can contain up to 16 carbon atoms. The term "alkyl" includes "bridged alkyl," i.e., a $C_6$–$C_{16}$ bicyclic or polycyclic hydrocarbon group, for example, norbornyl, adamantyl, bicyclo[2.2.2]octyl, bicyclc[2.2.1]heptyl, bicyclo[3.2.1]octyl, or decahydronaphthyl. The term "cycloalkyl" is defined as a cyclic $C_3$–$C_8$ hydrocarbon group, cyclopropyl, cyclobutyl, cyclohexyl, and cyclopentyl. The terms "alkenyl" and "alkynyl" are defined similarly to the term "alkyl," except the hydrocarbon group contains a carbon-carbon double bond or carbon-carbon triple bond, respectively.

The term "alkylene" refers to an alkyl group having a substituent. For example, the term "$C_{1-3}$alkylenearyl" refers to an alkyl group containing one to three carbon atoms and substituted with an aryl group. The term "alkenylene" as used herein is similarly defined, and contains the indicated number of carbon atoms and a carbon-carbon double bond, and includes straight chained and branched alkenylene groups, like ethyenylene.

The term "halo" or "halogen" is defined herein to include fluorine, bromine, chlorine, and iodine.

The term "haloalkyl" is defined herein as an alkyl group substituted with one or more halo substituents, either fluoro, chloro, bromo, iodo, or combinations thereof. Similarly, "halocycloalkyl" is defined as a cycloalkyl group having one or more halo substituents.

The term "aryl," alone or in combination, is defined herein as a monocyclic or polycyclic aromatic group, preferably a monocyclic or bicyclic aromatic group, e.g., phenyl or naphthyl, that can be unsubstituted or substituted, for example, with one or more, and in particular one to three, hydroxy, hydroxyalkyl, alkoxy, alkoxyalkyl, haloalkyl, nitro, amino, carboxy ($CO_2H$), $CO_2R^a$, alkylamino, acylamino, alkylthio, alkylsulfinyl, and alkylsulfonyl. Exemplary aryl groups include phenyl, naphthyl, tetrahydronaphthyl, 2-chlorophenyl, 3-chlorophenyl, 4-chlorophenyl, 2-methylphenyl, 4-methoxyphenyl, 3-trifluoromethylphenyl, 4-nitrophenyl, and the like. The terms "aryl$C_{1-3}$alkyl" and "heteroaryl$C_{1-3}$alkyl" are defined as an aryl or heteroaryl group having a $C_{1-3}$alkyl substituent.

The term "heteroaryl" is defined herein as a monocyclic or bicyclic ring system containing one or two aromatic rings and containing at least one nitrogen, oxygen, or sulfur atom in an aromatic ring, and which can be unsubstituted or substituted, for example, with one or more, and in particular one to three, substituents, like halo, alkyl, hydroxy, hydroxyalkyl, alkoxy, alkoxyalkyl, haloalkyl, nitro, amino, carboxy ($CO_2H$), $CO_2R^a$, alkylamino, acylamino, alkylthio, alkylsulfinyl, and alkylsulfonyl. Nonlimiting examples of heteroaryl groups include thienyl, furyl, pyridyl, oxazolyl, quinolyl, isoquinolyl, indolyl, triazolyl, tetrazolyl, isothiazolyl, isoxazolyl, imidizolyl, benzothiazolyl, pyrazinyl, pyrimidinyl, thiazolyl, and thiadiazolyl.

The term "Het" includes a 4- to 7-membered heterocycloalkyl group, including, but not limited to, morpholinyl, piperidyl, pyrrolidinyl, or piperazinyl.

The term "alkoxy" is defined as —OR, wherein R is alkyl.

The term "alkoxyalkyl" is defined as an alkyl group wherein a hydrogen has been replaced by an alkoxy group. The term "(alkylthio)alkyl" is defined similarly, except a sulfur atom, rather than an oxygen atom, is present.

The term "hydroxy" is defined as —OH.

The term "hydroxyalkyl"is defined as a hydroxy group appended to an alkyl group.

The term "amino" is defined as —$NH_2$, and the term "alkylamino" is defined as —$NR_2$, wherein at least one R is alkyl and the second R is alkyl or hydrogen.

The term "acylamino" is defined as RC(=O)N, wherein R is alkyl or aryl.

The term "alkylthio" is defined as —SR, where R is alkyl.

The term "alkylsulfinyl" is defined as R—$SO_2$, where R is alkyl.

The term "alkylsulfonyl" is defined as R—$SO_3$, where R is alkyl.

The term "nitro" is defined as —$NO_2$.

The term "trifluoromethyl" is defined as —$CF_3$.

The term "trifluoromethoxy" is defined as —$OCF_3$.

The term "cyano" is defined as —CN.

The term "spiro" as used herein refers to a group having two carbon atoms directly bonded to a carbon atom of the tetracyclic ring system.

In preferred embodiments, $R^4$ and $R^5$ are selected from the group consisting of $C_{1-6}$alkyl, $C_{1-6}$alkyleneC(=O)$OR^a$, C(=O)$OR^a$, C(=S)$NR^aR^b$, $C_{5-7}$spiro when combined with $R^3$, $C_{1-4}$alkyleneC(=O)$NR^aR^b$; $C_{1-4}$-alkylene$NR^aR^b$, $C_{1-4}$alkylene$OR^a$, $C_{1-4}$alkyleneSO$_2NR^aR^b$, $C_{1-4}$alkyleneheteroaryl, halo$C_{1-4}$alkyl, $C_{1-4}$alkyleneHet, $C_{1-4}$alkyleneC(=O)$C_{1-4}$alkyleneHet, and $C_{1-4}$alkylenearyl, and $R^a$ and $R^b$, independently, are selected from the group consisting of $C_{1-8}$alkyl, hydrogen, $C_{1-4}$alkylenearyl, Het, $C_{1-4}$alkyleneHet, $C_{3-8}$cycloalkyl, and halo$C_{1-6}$alkyl. Het, aryl, and heteroaryl can be substituted with one or more of C(=O)$OR^a$, $NR^aR^b$, and $C_{1-6}$alkyl.

In a more preferred group of compounds of formula (I), X is represented by $CH_2CH_2$, NH, or $NCH_3$; $R^3$ is hydrogen or methyl; and $R^4$ is selected from the group consisting of $C_{1-4}$alkyl, $C_{1-4}$alkyleneC(=O)$NH_2$, $C_{1-4}$alkyleneNH$_2$, $C_{1-4}$alkyleneC(=O)$OC_{1-7}$alkyl, $C_{1-6}$alkyleneC(=O)$OR^a$, $C_{1-3}$alkyleneOH, $C_{1-4}$alkyleneSO$_2NH_2$, $C_{1-4}$alkyleneOC$_{1-3}$alkylenearyl, halo$C_{1-3}$alkyl, $C_{1-3}$alkylenearyl, $C_{1-4}$alkyleneC(=O)OC$_{1-3}$haloalkyl,

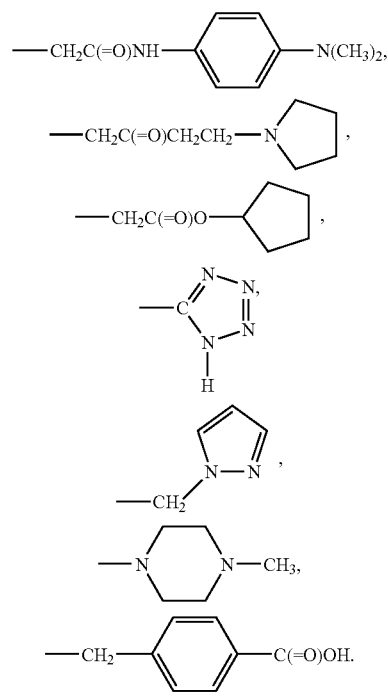

In another preferred embodiment, $R^3$ and $R^4$ are taken together to form a 5- or 6-membered spiro group.

A preferred $R^2$ group is represented by

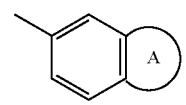

The bicyclic ring

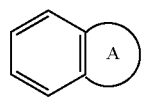

can represent, for example, naphthalene or indene, or a heterocyclic, such as benzoxazole, benzothiazole, benzisoxazole, benzimidazole, quinoline, indole, benzothiophene, or benzofuran, or

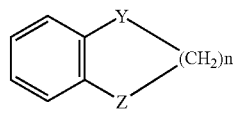

wherein n is an integer 1 or 2, and Y and Z, independently, represent $CH_2$, O, S, or $NR^a$. In a preferred group of compounds of formula (I), $R^2$ is represented by an optionally substituted bicyclic ring

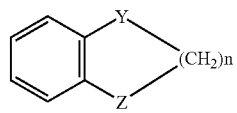

wherein n is 1 or 2, and Y and Z are each $CH_2$ or O. Especially preferred $R^2$ bicyclic rings include

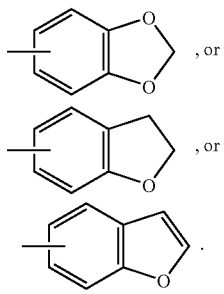

Within this particular group of compounds, nonlimiting examples of substituents are halogen (e.g., chlorine), hydroxy, $C_{1-3}$alkyl (e.g., methyl, ethyl, or i-propyl), $C_{1-3}$alkoxy (e.g., methoxy or ethoxy), $CO_2R^b$, halomethyl (e.g., trifluoromethoxy), cyano, nitro, and $NR^aR^b$.

An especially preferred subclass of compounds within the general scope of formula (I) is represented by compounds of formula (II)

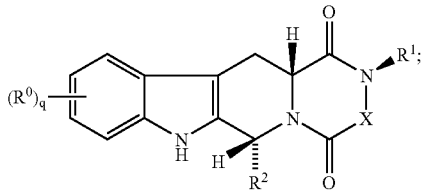

and pharmaceutically acceptable salts and solvates (e.g., hydrates) thereof.

Compounds of formula (I) can contain one or more asymmetric center, and, therefore, can exist as stereoisomers. The present invention includes both mixtures and separate individual stereoisomers of the compounds of formula (I). Compounds of formula (I) also can exist in tautomeric forms, and the invention includes both mixtures and separate individual tautomers thereof.

Pharmaceutically acceptable salts of the compounds of formula (I) can be acid addition salts formed with pharmaceutically acceptable acids. Examples of suitable salts include, but are not limited to, the hydrochloride, hydrobromide, sulfate, bisulfate, phosphate, hydrogen phosphate, acetate, benzoate, succinate, fumarate, maleate, lactate, citrate, tartrate, gluconate, methanesulfonate, benzenesulfonate, and p-toluenesulfonate salts. The compounds of the formula (I) also can provide pharmaceutically acceptable metal salts, in particular alkali metal salts and alkaline earth metal salts, with bases. Examples include the sodium, potassium, magnesium, and calcium salts.

Compounds of the present invention are potent and selective inhibitors of cGMP-specific PDE5. Thus, compounds of formula (I) are of interest for use in therapy, specifically for the treatment of a variety of conditions where selective inhibition of PDE5 is considered to be beneficial.

Phosphodiesterases (PDEs) catalyze the hydrolysis of cyclic nucleotides, such as cyclic adenosine monophosphate (cAMP) and cyclic guanosine monophosphate (cGMP). The PDEs have been classified into at least seven isoenzyme families and are present in many tissues (J. A. Beavo, *Physiol. Rev.*, 75, p. 725 (1995)).

PDE5 inhibition is a particularly attractive target. A potent and selective inhibitor of PDE5 provides vasodilating, relaxing, and diuretic effects, all of which are beneficial in the treatment of various disease states. Research in this area has led to several classes of inhibitors based on the cGMP basic structure (E. Sybertz et al., *Expert. Opin. Ther. Pat.*, 7, p. 631 (1997)).

The biochemical, physiological, and clinical effects of PDE5 inhibitors therefore suggest their utility in a variety of disease states in which modulation of smooth muscle, renal, hemostatic, inflammatory, and/or endocrine function is desirable. The compounds of formula (I), therefore, have utility in the treatment of a number of disorders, including stable, unstable, and variant (Prinzmetal) angina, hypertension, pulmonary hypertension, congestive heart failure, acute respiratory distress syndrome, acute and chronic renal failure, atherosclerosis, conditions of reduced blood vessel patency (e.g., postpercutaneous transluminal coronary or carotid angioplasty, or post-bypass surgery graft stenosis), peripheral vascular disease, vascular disorders, such as Raynaud's disease, thrombocythemia, inflammatory diseases, stroke, bronchitis, chronic asthma, allergic asthma, allergic rhinitis, glaucoma, osteoporosis, preterm labor, benign prostatic hypertrophy, peptic ulcer, male erectile dysfunction, female sexual dysfunction, and diseases characterized by disorders of gut motility (e.g., irritable bowel syndrome).

An especially important use is the treatment of male erectile dysfunction, which is one form of impotence and is a common medical problem. Impotence can be defined as a lack of power, in the male, to copulate, and can involve an inability to achieve penile erection or ejaculation, or both. The incidence of erectile dysfunction increases with age, with about 50% of men over the age of 40 suffering from some degree of erectile dysfunction.

In addition, a further important use is the treatment of female arousal disorder. Female arousal disorders are defined as a recurrent inability to attain or maintain an adequate lubrication/swelling response of sexual excitement until completion of sexual activity. The arousal response consists of vasocongestion in the pelvis, vaginal lubrication, and expansion and swelling of external genitalia.

It is envisioned, therefore, that compounds of formula (I) are useful in the treatment of male erectile dysfunction and female arousal disorder. Thus, the present invention concerns the use of compounds of formula (I), or a pharmaceutically acceptable salt thereof, or a pharmaceutical composition containing either entity, for the manufacture of a medicament for the curative or prophylactic treatment of erectile dysfunction in a male animal and arousal disorder in a female animal, including humans.

The term "treatment" includes preventing, lowering, stopping, or reversing the progression or severity of the condition or symptoms being treated. As such, the term "treatment" includes both medical therapeutic and/or prophylactic administration, as appropriate.

It also is understood that "a compound of formula (I)," or a physiologically acceptable salt or solvate thereof, can be administered as the neat compound, or as a pharmaceutical composition containing either entity.

Although the compounds of the invention are envisioned primarily for the treatment of sexual dysfunction in humans, such as male erectile dysfunction and female arousal disorder, they also can be used for the treatment of other disease states.

A further aspect of the present invention, therefore, is providing a compound of formula (I) for use in the treatment of stable, unstable, and variant (Prinzmetal) angina, hypertension, pulmonary hypertension, chronic obstructive pulmonary disease, congestive heart failure, acute respiratory distress syndrome, acute and chronic renal failure, atherosclerosis, conditions of reduced blood vessel patency (e.g., post-PTCA or post-bypass graft stenosis), peripheral vascular disease, vascular disorders such as Raynaud's disease, thrombocythemia, inflammatory diseases, prophylaxis of myocardial infarction, prophylaxis of stroke, stroke, bronchitis, chronic asthma, allergic asthma, allergic rhinitis, glaucoma, osteoporosis, preterm labor, benign prostatic hypertrophy, male and female erectile dysfunction, or diseases characterized by disorders of gut motility (e.g., IBS).

According to another aspect of the present invention, there is provided the use of a compound of formula (I) for the manufacture of a medicament for the treatment of the above-noted conditions and disorders.

In a further aspect, the present invention provides a method of treating the above-noted conditions and disorders in a human or nonhuman animal body which comprises administering to said body a therapeutically effective amount of a compound of formula (I).

Compounds of the invention can be administered by any suitable route, for example by oral, buccal, inhalation, sublingual, rectal, vaginal, transurethral, nasal, topical, percutaneous, i.e., transdermal, or parenteral (including intravenous, intramuscular, subcutaneous, and intracoronary) administration. Parenteral administration can be accomplished using a needle and syringe, or using a high pressure technique, like POWDERJECT™.

Oral administration of a compound of the invention is the preferred route. Oral administration is the most convenient and avoids the disadvantages associated with other routes of administration. For patients suffering from a swallowing disorder or from impairment of drug absorption after oral administration, the drug can be administered parenterally, e.g., sublingually or buccally.

Compounds and pharmaceutical compositions suitable for use in the present invention include those wherein the active ingredient is administered in an effective amount to achieve its intended purpose. More specifically, a "therapeutically effective amount" means an amount effective to prevent development of, or to alleviate the existing symptoms of, the subject being treated. Determination of the effective amounts is well within the capability of those skilled in the art, especially in light of the detailed disclosure provided herein.

A "therapeutically effective dose" refers to that amount of the compound that results in achieving the desired effect. Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index, which is expressed as the ratio between $LD_{50}$ and $ED_{50}$. Compounds which exhibit high therapeutic indices are preferred. The data obtained from such data can be used in formulating a dosage range for use in humans. The dosage of such compounds preferably lies within a range of circulating concentrations that include the $ED_{50}$ with little or no toxicity. The dosage can vary within this range depending upon the dosage form employed, and the route of administration utilized.

The exact formulation, route of administration, and dosage can be chosen by the individual physician in view of the patient's condition. Dosage amount and interval can be adjusted individually to provide plasma levels of the active moiety which are sufficient to maintain the therapeutic effects.

The amount of composition administered is dependent on the subject being treated, on the subject's weight, the severity of the affliction, the manner of administration, and the judgment of the prescribing physician.

Specifically, for administration to a human in the curative or prophylactic treatment of the conditions and disorders identified above, oral dosages of a compound of formula (I) generally are about 0.5 to about 1000 mg daily for an average adult patient (70 kg). Thus, for a typical adult patient, individual tablets or capsules contain 0.2 to 500 mg of active compound, in a suitable pharmaceutically acceptable vehicle or carrier, for administration in single or multiple doses, once or several times per day. Dosages for intravenous, buccal, or sublingual administration typically are 0.1 to 500 mg per single dose as required. In practice, the physician determines the actual dosing regimen which is most suitable for an individual patient, and the dosage varies with the age, weight, and response of the particular patient. The above dosages are exemplary of the average case, but there can be individual instances in which higher or lower dosages are merited, and such are within the scope of this invention.

For human use, a compound of the formula (I) can be administered alone, but generally is administered in admixture with a pharmaceutical carrier selected with regard to the intended route of administration and standard pharmaceutical practice. Pharmaceutical compositions for use in accordance with the present invention thus can be formulated in a conventional manner using one or more physiologically acceptable carriers comprising excipients and auxiliaries that facilitate processing of compounds of formula (I) into preparations which can be used pharmaceutically.

These pharmaceutical compositions can be manufactured in a conventional manner, e.g., by conventional mixing, dissolving, granulating, dragee-making, levigating, emulsifying, encapsulating, entrapping, or lyophilizing processes. Proper formulation is dependent upon the route of administration chosen. When a therapeutically effective amount of a compound of the present invention is administered orally, the composition typically is in the form of a tablet, capsule, powder, solution, or elixir. When administered in tablet form, the composition can additionally contain a solid carrier, such as a gelatin or an adjuvant. The tablet, capsule, and powder contain about 5 to about 95% compound of the present invention, and preferably from about 25 to about 90% compound of the present invention. When administered in liquid form, a liquid carrier such as water, petroleum, or oils of animal or plant origin can be added. The liquid form of the composition can further contain physiological saline solution, dextrose or other saccharide solutions, or glycols. When administered in liquid form, the composition contains about 0.5 to about 90% by weight of a compound of the present invention, and preferably about 1 to about 50% of a compound of the present invention.

When a therapeutically effective amount of a compound of the present invention is administered by intravenous, cutaneous, or subcutaneous injection, the composition is in the form of a pyrogen-free, parenterally acceptable aqueous solution. The preparation of such parenterally acceptable solutions, having due regard to pH, isotonicity, stability, and the like, is within the skill in the art. A preferred composition for intravenous, cutaneous, or subcutaneous injection typically contains, in addition to a compound of the present invention, an isotonic vehicle.

For oral administration, the compounds can be formulated readily by combining a compound of formula (I) with pharmaceutically acceptable carriers well known in the art. Such carriers enable the present compounds to be formulated as tablets, pills, dragees, capsules, liquids, gels, syrups, slurries, suspensions and the like, for oral ingestion by a patient to be treated. Pharmaceutical preparations for oral use can be obtained by adding a compound of formula (I) with a solid excipient, optionally grinding a resulting mixture, and processing the mixture of granules, after adding suitable auxiliaries, if desired, to obtain tablets or dragee cores. Suitable excipients include, for example, fillers and cellulose preparations. If desired, disintegrating agents can be added.

For administration by inhalation, compounds of the present invention are conveniently delivered in the form of an aerosol spray presentation from pressurized packs or a nebulizer, with the use of a suitable propellant. In the case of a pressurized aerosol, the dosage unit can be determined by providing a valve to deliver a metered amount. Capsules and cartridges of, e.g., gelatin, for use in an inhaler or insufflation can be formulated containing a powder mix of the compound and a suitable powder base such as lactose or starch.

The compounds can be formulated for parenteral administration by injection, e.g., by bolus injection or continuous infusion. Formulations for injection can be presented in unit dosage form, e.g., in ampules or in multidose containers, with an added preservative. The compositions can take such forms as suspensions, solutions, or emulsions in oily or aqueous vehicles, and can contain formulatory agents such as suspending, stabilizing, and/or dispersing agents.

Pharmaceutical formulations for parenteral administration include aqueous solutions of the active compounds in water-soluble form. Additionally, suspensions of the active compounds can be prepared as appropriate oily injection suspensions. Suitable lipophilic solvents or vehicles include fatty oils or synthetic fatty acid esters. Aqueous injection suspensions can contain substances which increase the viscosity of the suspension. Optionally, the suspension also can contain suitable stabilizers or agents that increase the solubility of the compounds and allow for the preparation of highly concentrated solutions. Alternatively, a present composition can be in powder form for constitution with a suitable vehicle, e.g., sterile pyrogen-free water, before use.

Compounds of the present invention also can be formulated in rectal compositions, such as suppositories or retention enemas, e.g., containing conventional suppository bases. In addition to the formulations described previously, the compounds also can be formulated as a depot preparation. Such long-acting formulations can be administered by implantation (for example, subcutaneously or intramuscularly) or by intramuscular injection. Thus, for example, the compounds can be formulated with suitable polymeric or hydrophobic materials (for example, as an emulsion in an acceptable oil) or ion exchange resins, or as sparingly soluble derivatives, for example, as a sparingly soluble salt.

Many of the compounds of the present invention can be provided as salts with pharmaceutically compatible counterions. Such pharmaceutically acceptable base addition salts are those salts that retain the biological effectiveness and properties of the free acids, and that are obtained by reaction with suitable inorganic or organic bases.

In particular, a compound of formula (I) can be administered orally, buccally, or sublingually in the form of tablets containing excipients, such as starch or lactose, or in capsules or ovules, either alone or in admixture with excipients, or in the form of elixirs or suspensions containing flavoring or coloring agents. Such liquid preparations can be prepared with pharmaceutically acceptable additives, such as suspending agents. A compound also can be injected parenterally, for example, intravenously, intramuscularly, subcutaneously, or intracoronarily. For parenteral administration, the compound is best used in the form of a sterile aqueous solution which can contain other substances, for example, salts, or monosaccharides, such as mannitol or glucose, to make the solution isotonic with blood.

For veterinary use, a compound of formula (I) or a nontoxic salt thereof, is administered as a suitably acceptable formulation in accordance with normal veterinary practice. The veterinarian can readily determine the dosing regimen and route of administration that is most appropriate for a particular animal.

Thus, the invention provides in a further aspect a pharmaceutical composition comprising a compound of the formula (I), together with a pharmaceutically acceptable diluent or carrier therefor. There is further provided by the present invention a process of preparing a pharmaceutical composition comprising a compound of formula (I), which process comprises mixing a compound of formula (I), together with a pharmaceutically acceptable diluent or carrier therefor.

In a particular embodiment, the invention includes a pharmaceutical composition for the curative or prophylactic treatment of erectile dysfunction in a male animal, or arousal disorder in a female animal, including humans, comprising a compound of formula (I) or a pharmaceutically acceptable salt thereof, together with a pharmaceutically acceptable diluent or carrier.

Compounds of formula (I) can be prepared by any suitable method known in the art, or by the following processes which form part of the present invention. In the methods below, $R^0$ through $R^5$, $R^a$, $R^b$, and X are as defined in structural formula (I) above. In particular, Daugan U.S. Pat. No. 5,859,006, incorporated herein by reference, discloses preparation of a compound of structural formula (III).

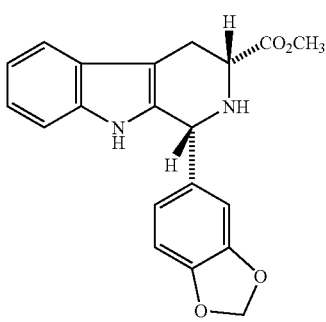

(III)

In short, the compound of structural formula (III), i.e., the cis-isomer of Intermediates 1 and 2 of Daugan U.S. Pat. No. 5,859,006 was prepared according to the following reaction scheme:

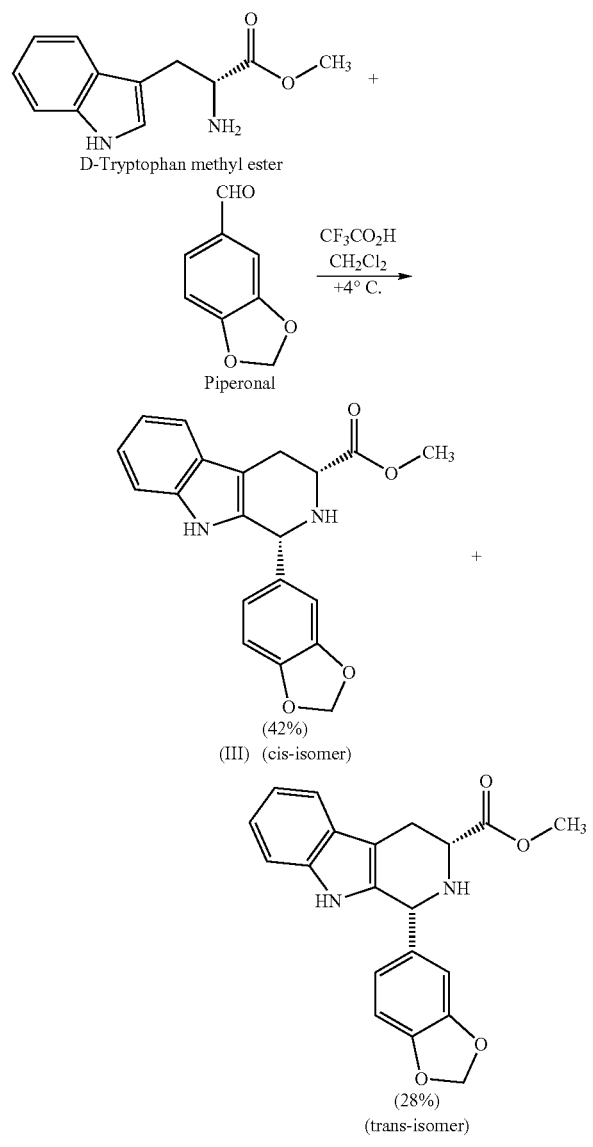

A compound of structural formula (I) is prepared similarly by reacting a tryptophan ester, or a tryptophan ester substituted with suitable $R^0$ substituents, with a suitable aldehyde to provide the desired $R^2$ substituent. The resulting product then is cyclized by reaction with a suitable amine to provide a compound of structural formula (I). The cyclization reaction is disclosed in Daugan U.S. Pat. No. 5,859,006.

In the synthesis of compounds of structural formula (I), protecting compounds and protecting groups, like benzyl chloroformate and trichloroethyl chloroformate, which are well known to persons skilled in the art, can be used. Such protecting groups are disclosed, for example, in T. W. Greene et al. "Protective Groups in Organic Synthesis, Third Edition," John Wiley and Sons, Inc., NY, N.Y. (1999). These protecting groups are removed in the final steps of the synthesis under basic, acidic, or hydrogenolytic conditions which are readily apparent to those skilled in the art. By employing appropriate manipulation and protection of chemical functionalities, synthesis of compounds of structural formula (I) not specifically set forth herein can be accomplished by methods analogous to the schemes set forth below. For example, the structure of a compound of structural formula (I) can be varied by using an appropriate aldehyde to change the identity of $R^2$, or by using a halo or alkyl phenyl-substituted tryptophan ester.

Compounds of formula (I) can be converted to other compounds of formula (I). Thus, for example, when a compound contains a substituted aromatic ring, it is possible to prepare another suitably substituted compound of formula (I). Examples of appropriate interconversions include, but are not limited to, $OR^a$ to hydroxy by suitable means (e.g., using a agent such as $SnCl_2$ or a palladium catalyst, such as palladium-on-carbon), or amino to substituted amino, such as alkylamine, using standard acylating or sulfonylating conditions.

Compounds of structural formula (I) can be made accordingly to one of the following four nonlimiting synthetic routes.

Method A

The 1,2,3,4-tetrahydro-β-carbolines of general formula (IV) can be prepared by the Pictet-Spengler reaction as set forth in Daugan U.S. Pat. No. 5,859,006 and in A. Madrigal et al., *J. Org. Chem.*, 63, page 2724 (1998), for example. The resulting secondary amine then is treated with either an amino acid or an acid halide, under suitable acylation conditions, to form an amideester. Ring cyclization to form the diketopiperazine (I) is accomplished by intramolecular amine attack on the ester. The amine can be derived from a suitable side chain bearing a leaving group that reacts with primary amine compound (V).

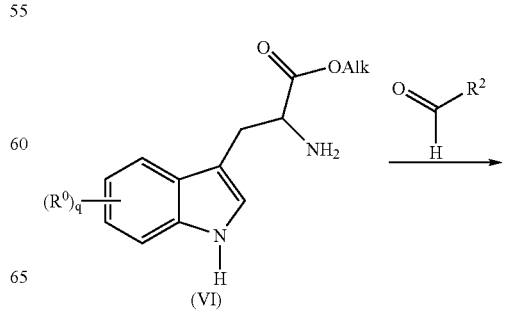

(VI)

-continued

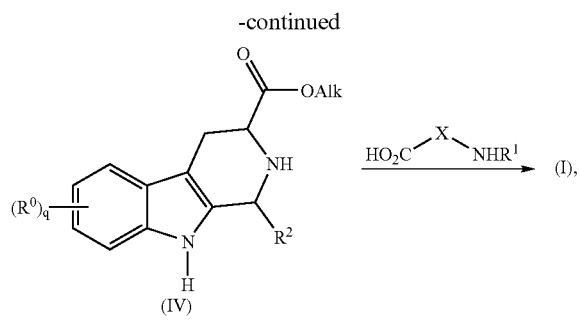

or

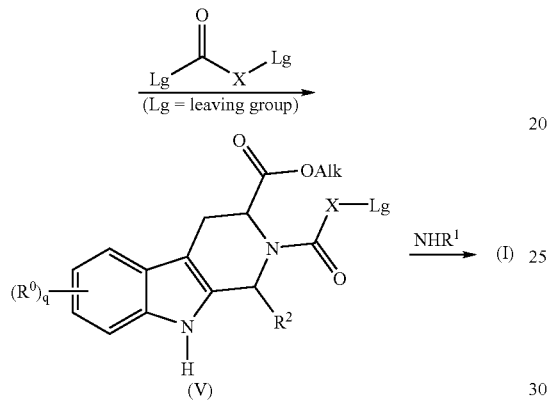

Method B

The diketopiperazine (I) also can be prepared by reaction of a tryptophan with an amino acid under typical peptide coupling conditions to form an N-acyltryptophan. Ring cyclization to form diketopiperazine (I) is accomplished by intramolecular amine attack on the ester. The resulting piperazine can undergo a condensation with an aldehyde under modified Pictet-Spengler conditions (see T. A. Miller et al., *Bioorg. Med. Chem. Lett.*, 8, p. 1065 (1998), for example) to give the β-carboline.

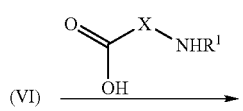

-continued

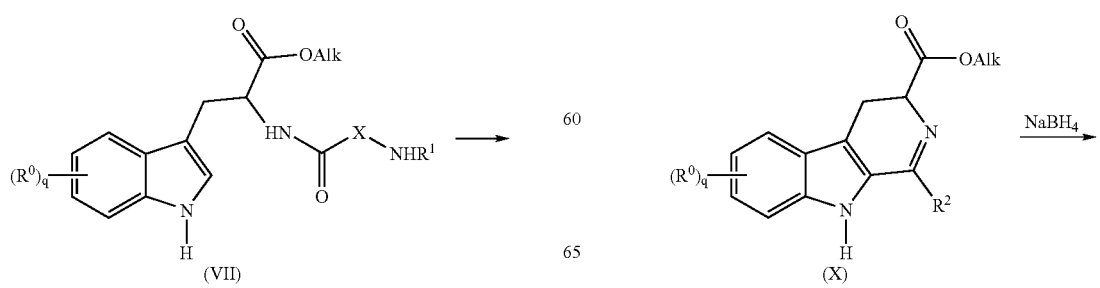

Method C

The β-carboline skeleton also can be prepared using the Bischler-Napieralski reaction, which is a cyclodehydration of an acylated tryptophan, as disclosed in W. M. Whaley et al., *Org. React., VI, pp.* 74–150 (1951). $P_2O_5$ and $POCl_3$ are the most common cyclization reagents. Reduction of the imine with $NaBH_4$, for example, yields the 1,2,3,4-tetrahydro-β-carboline.

A modified method, which avoids the potential for racemisation, includes acylating the amine of tryptophan first, followed by conversion to the thioamide with, for example, with Lawesson's reagent. Treatment of the thioamide with an alkyl halide or acyl halide provides the iminium halide. Reduction of the crude iminium halide with sodium borohydride ($NaBH_4$) at reduced temperature stereo-selectively provides the 1,2,3,4-tetrahydro-β-carboline.

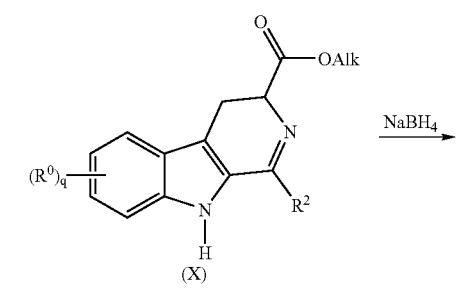

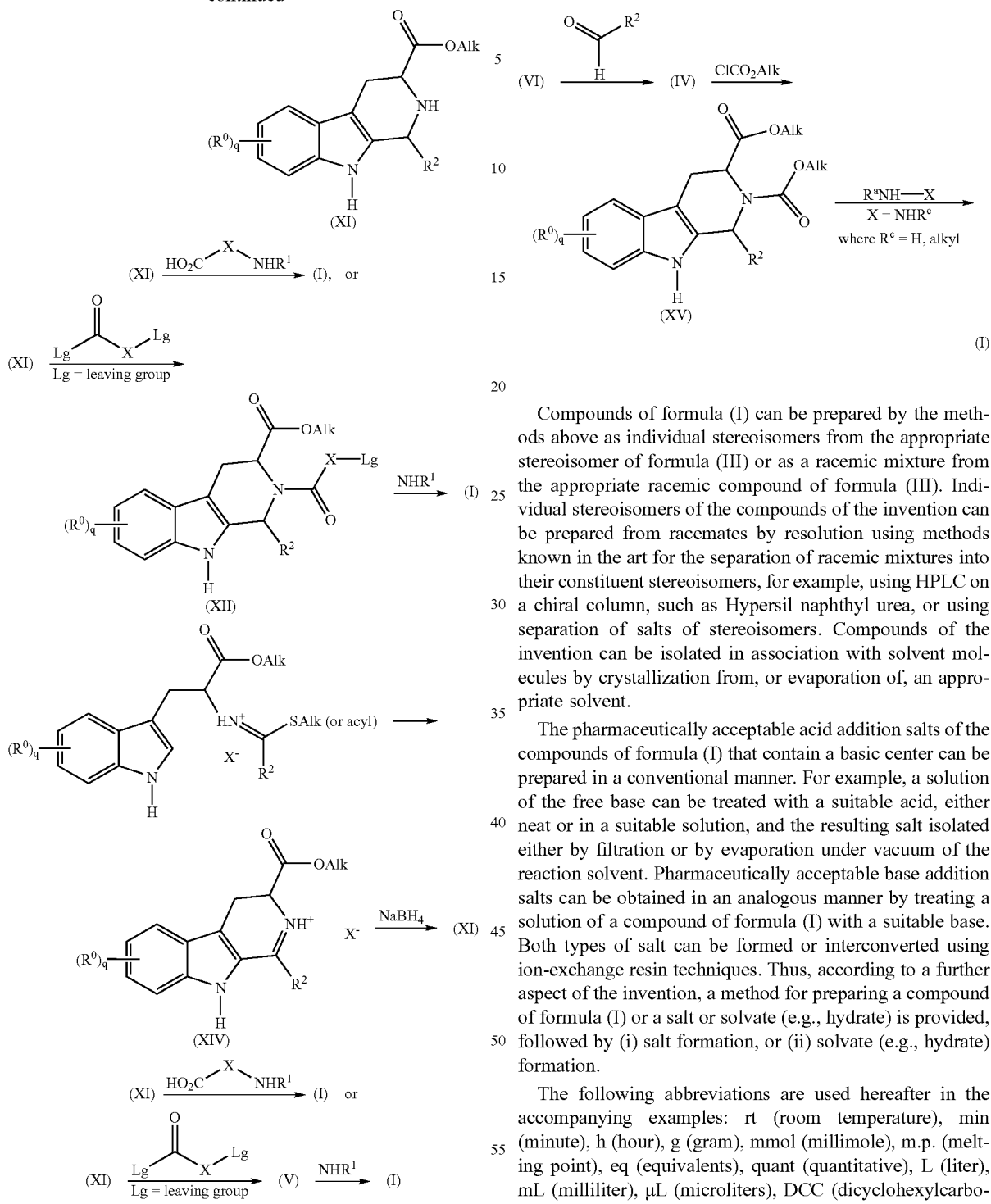

Method D

In addition, the β-carboline can be treated with a chloroformate to form a 2,3-dicarboxylic acid diester. Treatment of the diester with, for example, a hydrazine, provides compounds of general formula (I) when X contains nitrogen (see K. Winterfield et al., *Arch. Pharmaz,* 304, 216 (1971) and E. H. White et al., *J. Org. Chem.,* 32, 1921 (1967).

Compounds of formula (I) can be prepared by the methods above as individual stereoisomers from the appropriate stereoisomer of formula (III) or as a racemic mixture from the appropriate racemic compound of formula (III). Individual stereoisomers of the compounds of the invention can be prepared from racemates by resolution using methods known in the art for the separation of racemic mixtures into their constituent stereoisomers, for example, using HPLC on a chiral column, such as Hypersil naphthyl urea, or using separation of salts of stereoisomers. Compounds of the invention can be isolated in association with solvent molecules by crystallization from, or evaporation of, an appropriate solvent.

The pharmaceutically acceptable acid addition salts of the compounds of formula (I) that contain a basic center can be prepared in a conventional manner. For example, a solution of the free base can be treated with a suitable acid, either neat or in a suitable solution, and the resulting salt isolated either by filtration or by evaporation under vacuum of the reaction solvent. Pharmaceutically acceptable base addition salts can be obtained in an analogous manner by treating a solution of a compound of formula (I) with a suitable base. Both types of salt can be formed or interconverted using ion-exchange resin techniques. Thus, according to a further aspect of the invention, a method for preparing a compound of formula (I) or a salt or solvate (e.g., hydrate) is provided, followed by (i) salt formation, or (ii) solvate (e.g., hydrate) formation.

The following abbreviations are used hereafter in the accompanying examples: rt (room temperature), min (minute), h (hour), g (gram), mmol (millimole), m.p. (melting point), eq (equivalents), quant (quantitative), L (liter), mL (milliliter), µL (microliters), DCC (dicyclohexylcarbodiimide), Cbz (benzylcarbamate), DMSO (dimethyl sulfoxide), $CH_2Cl_2$ (dichloromethane), $CHCl_3$ (chloroform), IPA (isopropyl alcohol), TFA (trifluoroacetic acid), EtOH (ethanol), AcOH (acetic acid), EtOAc (ethyl acetate), MeOH (methanol), $Et_3N$ (triethylamine), DMF (dimethylformamide), EtOAc (ethyl acetate), and THF (tetrahydrofuran).

The following illustrates specific examples of compounds of structural formula (I) and synthetic routes to some of these structures.

Preparation of Example 1

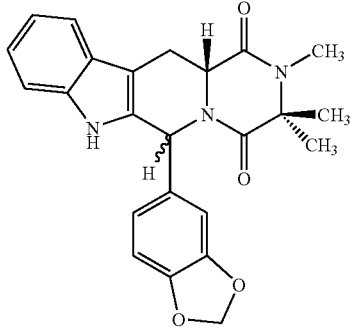

EXAMPLE 1

Example 1 was prepared from a tryptophan ester (Intermediate 1). The tryptophan ester utilized to prepare Example 1 is available commercially from Aldrich Chemical Co., Milwaukee, Wis. The Pictet-Spengler reaction to provide Example 1 from Intermediate 4 is disclosed in T. A. Miller et al., *Bioorg. Med. Chem. Lett.*, 8, 1065 (1998); J. J. Tepe et al., *J. Med. Chem.*, 39, 2188 (1996); C. W. Ong et al., *Aust. J. Chem.*, 43, 773 (1990); and R. H. Herbert et al., *Tetrahedron Lett.*, 35, 5497 (1994).

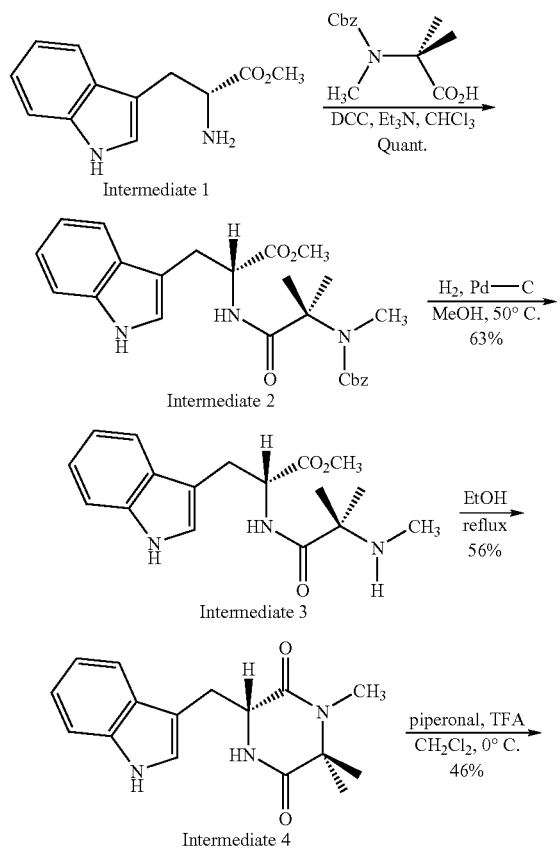

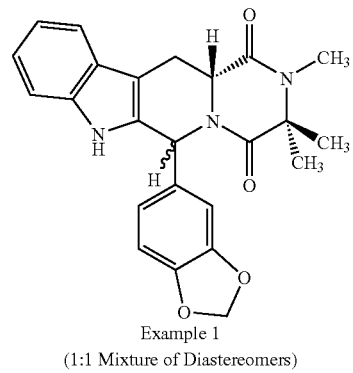

Example 1
(1:1 Mixture of Diastereomers)

Preparation of Cbz-Protected Amide Intermediate 2

Dicyclohexylcarbodiimide (1.8 g, 8.8 mmol) was added to a solution of N-Cbz-N,2-dimethylalanine (2.0 g, 8.0 mmol) in methylene chloride (10 mL) at 0° C. under a nitrogen blanket in one portion. The resulting white slurry was stirred at 0° C. for 30 min, after which a slurry of Intermediate 1 (1.7 g, 8.0 mmol) and triethylamine (1.3 mL, 10 mmol) in methylene chloride (10 mL) was added over 5 min. The resulting white slurry was slowly warmed to room temperature, then stirred for a total of 6 days. The slurry then was filtered under reduced pressure, and the solid was washed with $CH_2Cl_2$ (50 mL). The filtrate was concentrated under reduced pressure to provide a yellow oil, which was purified by flash column chromatography, eluting with ethyl acetate/chloroform (1:9), to provide Cbz-protected amide Intermediate 2 as a white semi-solid (3.76 g, 100%): TLC $R_f$ (1:4 ethyl acetate/chloroform)=0.35; $^1$H NMR (300 MHz, DMSO-$d_6$): δ10.85 (s, 1H), 7.76 (d, J=7.6 Hz, 1H), 7.46 (d, J=7.6 Hz, 1H), 7.34–7.26 (m, 5H), 7.12 (s, 1H), 7.06–6.94 (m, 2H), 4.88–4.83 (m, 1H), 4.46 (q, J=8.0 Hz, 1H), 3.53 (s, 3H), 3.09 (t, J=6.5 Hz, 2H), 2.89 (2, 3H), 1.29 (s, 3H), 1.23 (s, 3H) ppm.

Preparation of Methylamine Intermediate 3

A solution of Intermediate 2 (3.7 g, 8.2 mmol) in acetic acid (10 mL) and methanol (50 mL) was treated with a catalytic amount of 10% palladium on carbon (0.40 g, 50% wet) and the resulting mixture was stirred under a hydrogen atmosphere at 50° C. for 29 hours. The reaction mixture then was cooled to room temperature, and the palladium catalyst was removed by vacuum filtration through a plug of Celite. The filtrate was concentrated under reduced pressure to provide a yellow residue, which was purified by flash column chromatography, eluting with methanol/chloroform (1:9), to provide Intermediate 3 as an amber oil (1.65 g, 65%): TLC $R_f$ (1:9 methanol/chloroform)=0.55; $^1$H NMR (300 MHz, CDCl$_3$): δ8.17 (s, 1H), 7.70 (d, J=7.9 Hz, 1H), 7.59 (d, J=7.8 Hz, 2H), 7.35 (d, J=7.7 Hz, 1H), 7.19–7.12 (m, 2H), 4.87 (q, J=5.3 Hz, 1H), 3.72 (s, 3H), 3.37–3.30 (m, 2H), 2.27 (s, 3H), 1.38 (s, 3H), 1.33 (s, 3H) ppm; API MS m/z 318 $[C_{17}H_{23}N_3O_3+H]^+$.

Preparation of Diketopiperazine Intermediate 4

A suspension of Intermediate 3 (1.6 g, 5.0 mmol) in ethanol (50 mL) was heated to reflux under a nitrogen blanket and stirred for a total of 3 days. The solvent was removed under reduced pressure to provide a residue which was purified by flash column chromatography, eluting with methanol/chloroform (1:19), to provide diketopiperazine Intermediate 4 as a white foam (0.810 g, 56%): mp 223–229° C.; TLC $R_f$ (1:9 methanol/chloroform)=0.63; $^1$H NMR (300 MHz, DMSO-$d_6$): δ10.86 (s, 1H), 8.12 (s, 1H), 7.50 (d, J=7.9 Hz, 1H), 7.28 (d, J=8.0 Hz, 1H), 7.01–6.93 (m, 3H), 4.19 (s, 1H), 3.29–3.28 (m, 1H), 2.98 (dd, J=4.6, 14.2 Hz, 1H), 2.57 (s, 3H), 1.22 (s, 6H) ppm; CI MS (methane) m/z 286 $[C_{16}H_{19}N_3O_2+H]^+$; $[\alpha]_D^{25°\ C.}=-26.5°$ (c=0.10, DMSO).

Preparation of Example 1

(12a,R)-6-Benzo[1,3]dioxol-5-yl,2,3,3-trimethyl-2,3,6,7,12,12a-hexahydropyrazino[1',2':1,6]-pyrido[3,4-b]indole-1,4-dione Trifluoroacetic acid (0.5 mL, 6.2 mmol) was added to a suspension of Intermediate 4 (0.800 g, 2.8 mmol) and piperonal (0.505 g, 3.4 mmol) in methylene chloride (10 mL) at 0° C. under a nitrogen blanket, after which the solution was warmed to room temperature and stirred for a total of 22 hours. The reaction mixture was diluted with ethyl acetate (150 mL), washed with saturated sodium bicarbonate (NaHCO$_3$) solution (100 mL) and brine (50 mL), treated with silica gel (5 g), then the solvent was removed under reduced pressure. The residue was purified by flash column chromatography, eluting with methanol/chloroform (1:49), to provide Example 1 as a white powder (0.534 g, 46%, 1:1 mixture of cis and trans diastereomers at C6): mp 225–235° C.; TLC $R_f$ (1:19 methanol/chloroform)=0.87; $^1$H NMR (300 MHz, DMSO-$d_6$): δ10.08 (s, 2H), 8.37 (s, 1H), 8.25 (s, 1H), 7.46 (t, J=8.9 Hz, 2H), 7.28 (t, J=8.2 Hz, 2H), 7.02–6.95 (m, 4H), 6.80 (d, J=8.0 Hz, 2H), 6.60 (s, 1H), 6.48 (d, J=8.1 Hz, 1H), 6.15 (s, 1H), 5.98 (d, J=4.4 Hz, 2H), 4.19 (s, 2H), 3.22 (dd, J=3.9, 14.8 Hz, 2H), 3.00–2.89 (m, 2H), 2.70 (s, 3H), 2.62 (s, 3H), 1.35 (s, 3H), 1.31 (s, 3H), 0.65 (s, 3H), 0.47 (s, 3H) ppm; API MS m/z 418 $[C_{24}H_{23}N_3O_4+H]^+$; $[\alpha]_D^{25°\ C.}=-63.1°$ (c=0.50, CHCl$_3$). Anal. Calcd. for $C_{24}H_{23}N_3O_4$: C, 69.05; H, 5.55; N, 10.07. Found: C, 68.91; H, 5.56; N, 10.04. Chiral HPLC analysis (Chiralcel OD Column, 250×4.6 mm, Retention Time=7.34 min; 1:1 isopropanol/hexanes; flow=0.5 mL/min; detector @ 254 nm; 25° C.) showed one major peak, with a purity of 99.9%.

Preparation of Example 2

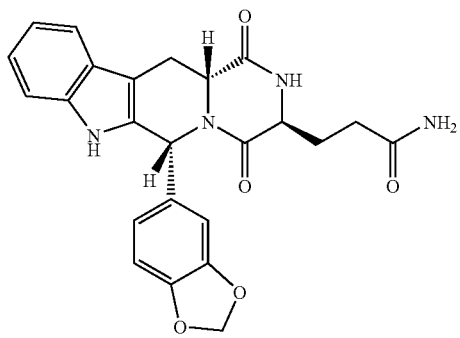

Example 2 was prepared from the compound of structural formula (III) and N-Cbz-L-glutamine as illustrated below.

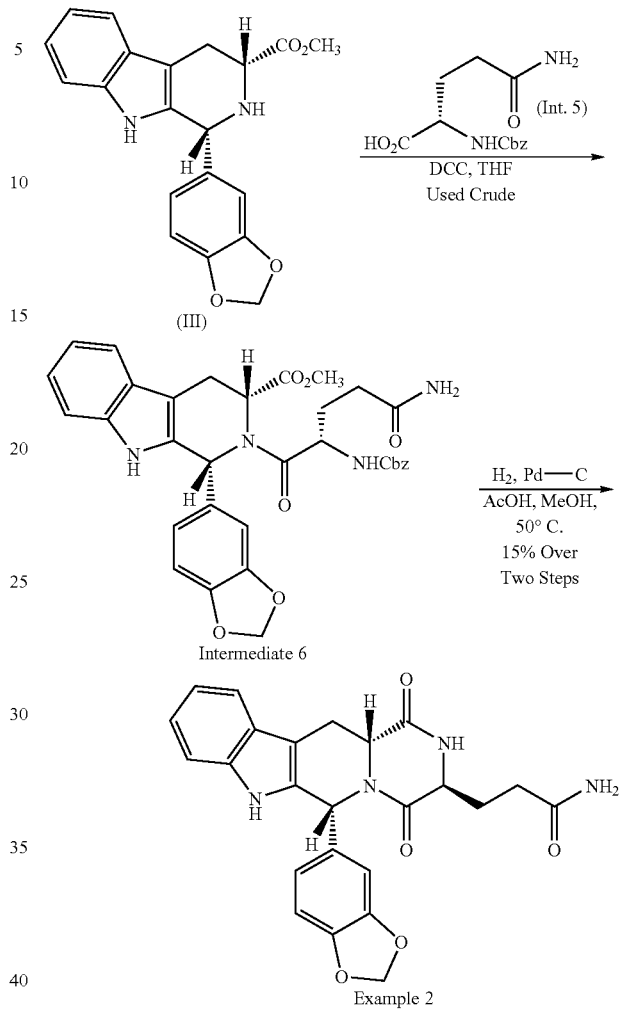

Preparation of cis-β-Carboline Amide Intermediate 6

To a solution of N-Cbz-L-glutamine (Intermediate 5) (5.0 g, 17.8 mmol) in THF (80 mL) at 0° C. under a nitrogen blanket was added dicyclohexylcarbodiimide (4.4 g, 21.4 mmol) in one portion. The resulting white slurry was stirred at 0° C. for 30 minutes, after which Compound (III) (6.3 g, 17.8 mmol) was added in one portion. The resulting amber slurry was slowly warmed to room temperature, then stirred 48 hours. The slurry was filtered under reduced pressure and the solid was washed with methylene chloride (500 mL). The filtrate was concentrated under reduced pressure to provide an amber foam, which was partially purified by flash column chromatography, eluting with methanol/chloroform (1:9), to provide Intermediate 6 as an off-white foam (4.6 g): TLC $R_f$ (9:1 methanol/chloroform)=0.60.

Preparation of Example 2

3-((3S,6R,12aR)-6-Benzo[1,3]dioxol-5-yl-1,4-dioxo-1,2,3,4,6,7,12,12a-octahydropyrazino[1',2':1,6]-pyrido[3,4-b]indo-3-yl)propionamide A solution of Intermediate 6 (4.6 g, 7.5 mmol) in methanol (50 mL) and acetic acid (5 mL) was treated with a catalytic amount of 10% palladium on carbon (500 mg, 50% wet) and the resulting mixture was stirred under a hydrogen atmosphere at 50° C. for 3 hours. The reaction mixture then was cooled to room temperature and the palladium catalyst was removed by vacuum filtration through Celite (10 g). The filtrate was concentrated under reduced pressure and the residue was purified by flash column chromatography, eluting with methanol/chloroform (1:9), to provide Example 2 as a white powder (1.24 g, 15% over two steps): mp 78–82° C.; TLC $R_f$ (4:1 chloroform/methanol)=0.58; $^1$H NMR (300 MHz, DMSO-$d_6$): δ11.05 (s, 1H), 8.57 (d, J=3.8 Hz, 1H), 7.52 (d, J=7.3 Hz, 1H), 7.30 (d, J=7.7 Hz, 1H), 7.23 (s, 1H), 7.08–6.97 (m, 2H), 6.78 (s, 1H), 6.10 (s, 1H), 5.92 (s, 2H), 4.43 (dd, J=4.4, 11.4 Hz, 1H), 3.83–3.80 (m, 1H), 3.61 (dd, J=4.5, 15.8 Hz, 1H), 3.32 (s, 3H), 2.93 (dd, J=11.7, 15.8 Hz, 1H), 2.17 (t, J=7.2 Hz, 2H), 1.94 (t, J=7.4 Hz, 2H) ppm; API MS m/z 447 $[C_{24}H_{22}N_4O_5+H]^+$. Anal. Calcd. for $C_{24}H_{22}N_4O_5 \cdot H_2O$: C, 62.06; H, 5.21; N, 12.06. Found: C, 62.12; H, 5.00; N, 12.07. The relative stereochemistry of analog Example 2 was confirmed to be the cis isomer by a series of NOE difference experiments: positive NOE enhancements from the C12a proton at 4.45 ppm to the $C_6$ proton at 6.10 ppm; a positive NOE enhancement from the C6 proton at 6.10 ppm to the C12a proton at 4.45 ppm.

Preparation of Example 3

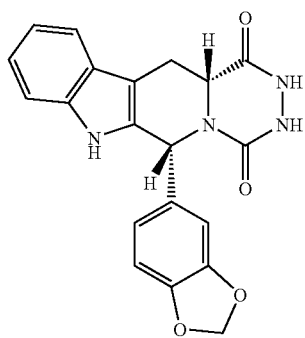

Example 3 was prepared from the hydrochloride of Compound (III) by the following synthetic sequence. The 1,2,4-triazine-3,6-dione of Example 3 was prepared by the method of K. Winterfield et al., *Arch. Pharmaz.*, 304, 0. 216 (1971).

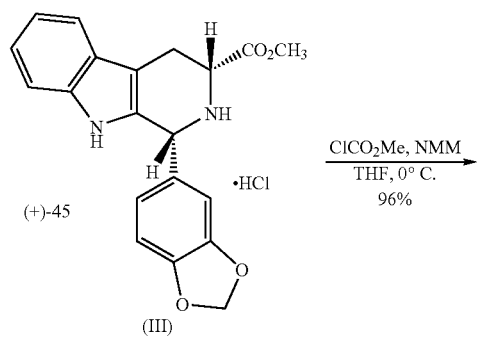

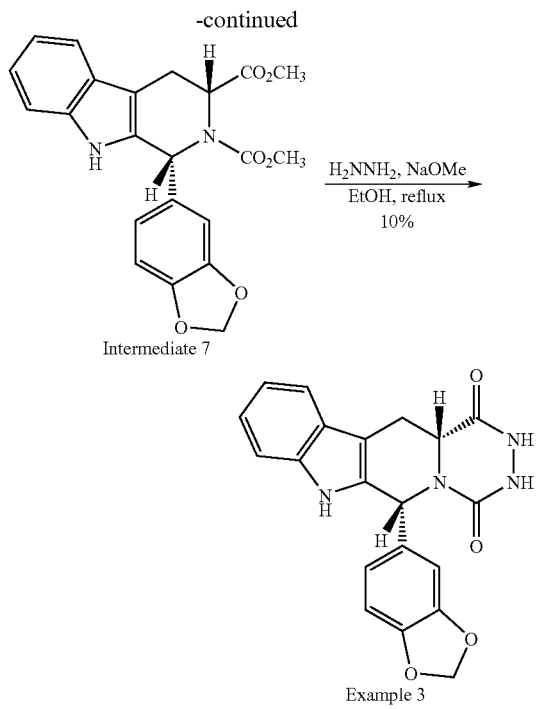

Preparation of cis-β-Carboline Carbamate Intermediate 7

Methyl chloroformate (4.8 mL, 62 mmol) was added dropwise to a suspension of Compound (III) (20 g, 52 mmol) and N-methylmorpholine (14.2 mL, 129 mmol) in THF (150 mL) at 0° C. under a nitrogen blanket. The mixture was slowly warmed to room temperature, then stirred for 3 days. The resulting mixture was diluted with ethyl acetate (200 mL), washed with brine (150 mL), dried over magnesium sulfate ($MgSO_4$), and filtered. The solvent was removed under reduced pressure to afford Intermediate 7 as an amber foam (21 g, 96%), which was suitable for use without further purification.

Preparation of Example 3

(5aR,10R)-10-Benzo[1,3]dioxol-5-yl-5,5a,7,8,10,11-hexahydro-7,8,9a,11-tetraazabenzo[b]fluorene-6,9-dione Sodium methoxide (5.2 mL, 27 mmol, 30% solution in methanol) was added dropwise to a mixture of Intermediate 7 (5 g, 12 mmol) and anhydrous hydrazine (0.5 mL, 15 mmol) in ethanol (30 mL), and the mixture was heated at reflux under a nitrogen blanket for 27 hours. The suspension was cooled to room temperature and the orange solids were removed by vacuum filtration. The organic phase was concentrated under reduced pressure to afford an oxange foam which was purified by reverse phase flash column chromatography on C-18 silica gel, elutinq with methanol/water (1:2), to provide the crude product as an orange oil. The oil was further purified by flash column chromatography, eluting with methanol/chloroform (1:4), to provide Example 3 as a yellow powder (0.465 g, 10%): mp 188–194° C.; TLC $R_f$ (1:4 methanol/chloroform)=0.37; $^1$H NMR (300 MHz, $D_2O$): δ7.72 (d, J=7.6 Hz, 1H), 7.42 (t, J=8.6 Hz, 1H), 7.30–7.23 (m, 2H), 7.00 (s, 1H), 6.23–6.83 (m, 1H), 6.04 (d, J=11.1 Hz, 2H), 5.73 (s, 1H), 4.18 (dd, J=7.0, 11.5 Hz, 1H), 3.51 (dd, J=5.0, 11.4 Hz, 1H), 3.22 (t, J=15.3 Hz, 1H) ppm; API MS m/z 377 [$C_{20}H_{16}N_4O_4$+H]$^+$; [α]$_D^{25\ °C}$=+44.7° (c=0.5, methanol). Anal. Calcd. for $C_{20}H_{16}N_4O_4 \cdot 0.25\ H_2O$: C, 63.07; H, 4.37; N, 14.71. Found: C, 63.06; H, 4.30; N, 14,71. The relative stereochemistry of Example 3 was confirmed to be the cis isomer by a series of NOE difference experiments: a positive NOE enhancement from the C12a proton at 3.57 ppm to the C6 proton at 5.73 ppm; a positive NOE enhancement from the C6 proton at 5.73 ppm to the C12a proton at 3.57 ppm.

Preparation of Example 4

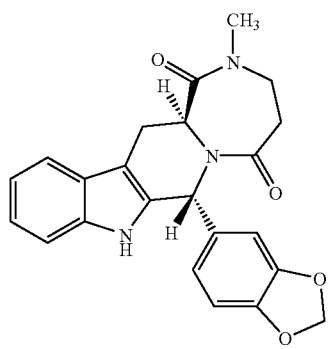

The compound of Example 4 was prepared from Compound (III) by the following reaction scheme.

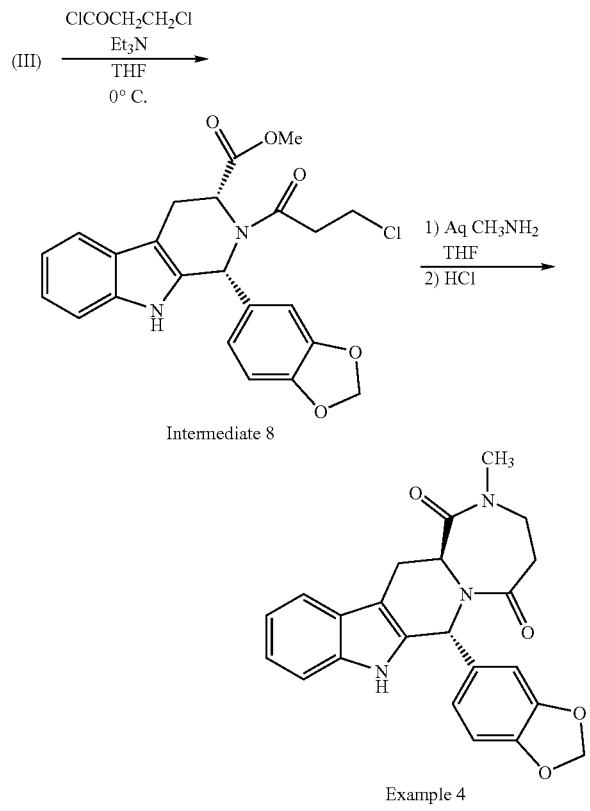

Preparation of (+)-cis-3-Chloropropionyl-β-Carboline Intermediate 8

To a mixture of Compound (III) (6.00 g, 15.5 mmol) and triethylamine (6.5 mL, 46.5 mmol) in THF (100 mL) and water (25 mL), was added 3-chloropropionyl chloride (1.9 mL, 20.2 mmol), dropwise, at 0° C. under a nitrogen blanket. The resulting mixture was warmed to room temperature and stirred for 1.5 hours. The reaction was quenched with 1 N HCl (40 mL) and was concentrated to remove THF. The residue was diluted with EtOAc (200 mL), then the layers were separated. The organic phase was washed with 1 N HCl (50 mL), saturated NaHCO$_3$ (50 mL), and saturated sodium chloride (NaCl) (50 mL), then dried over anhydrous Na$_2$SO$_4$. Filtration and concentration in vacuo gave an oil which was purified by column chromatography (silica gel, 0–5% EtOAc/CH$_2$Cl$_2$). The product was obtained as a pale yellow foam 2.30 g (33.6%): TLC R$_f$ (90:10:1/CH$_2$Cl$_2$:EtOAc:MeOH)=0.80; $^1$H NMR (300 MHz, CDCl): δ10.86 (s, 1H), 7.54 (d, J=7.6 Hz, 1H), 7.28 (d, J=7.9 Hz, 1H), 7.10 (t, J=7.4 Hz, 1H), 7.02 (t, J=7.3 Hz, 1H), 6.85 (s, 1H), 6.79 (d, J=8.1 Hz, 1H), 6.67 (s, 1H), 6.44 (d, J=8.0 Hz, 1H), 6.27 (s, 1H), 5.97 (d, J=4.5 Hz, 2H), 5.28 (d, J=6.6 Hz, 1H), 3.90 (t, J=6.5 Hz, 2H), 3.43 (d, J=16.0 Hz, 1H), 3.17–3.37 (m, 2H), 2.91–3.06 (m, 4H).

Preparation of Example 4

(5aS,11R)-11-Benzo[1,3]dioxol-5-yl-7-methyl-5,5a,8,9,11,12-hexahydro-7H-7,10a,12-triaza-cyclohepta[b]fluorene-6,10-dione A mixture of Intermediate 8 (1.22 g, 2.77 mmol), 40% methylamine in water (1.2 mL, 13.8 mmol), and THF (20 mL) was stirred at 45° C. under a nitrogen blanket. After 4 hours, only starting material and the 3-methylamino intermediate were detected. Sodium iodide (20.7 mg, 0.138 mmol) and 40% methylamine in water (1.2 mL) were added, and the mixture was stirred at 45° C. for 4 days. The mixture was cooled to room temperature and was quenched with 1 N HCl (2 mL). The residue was diluted with CH$_2$Cl$_2$ (100 mL), washed with 0.1 N HCl (10 mL), water (30 mL), and saturated NaCl (20 mL), then dried over anhydrous Na$_2$SO$_4$. Filtration and concentration in vacuo gave a yellow foam which as purified by column chromatography (silica gel, 90:10:1/CH$_2$Cl$_2$:EtOAc:MeOH). The product was obtained as a white solid 0.55 g (49.5%) after recrystallization from MeOH/water. The product was contaminated with approximately 8% of the cis isomer: mp 179–182° C.; TLC R$_f$ (90:10:1/CH$_2$Cl$_2$:EtOAc:MeOH)=0.27; $^1$H NMR (300 MHz, DMSO-d$_6$): δ 11.08 (s, 1H), 7.48 (d, J=7.7 Hz, 1H), 7.32 (d, J=7.9 Hz, 1H), 7.10 (t, J=7.5 Hz, 1H), 7.01 (t, J=7.2 Hz, 1H), 6.86 (d, J=8.0 Hz, 1H), 6.83 (s, 1H), 6.79 (d, J=1.5 Hz, 1H), 6.59 (d, J=8.7 Hz, 1H), 6.01 (d, J=2.3 Hz, 2H), 4.45 (dd, J=4.1 Hz, J=11.0 Hz, 1H), 3.74–3.82 (m, 1H), 3.27–3.45 (m, 2H), 3.08 (dd, J=4.1 Hz, J=15.4 Hz, 1H), 2.91–3.00 (m, 4H), 2.74–2.81 (m, 1H); MS (API) m/z 404 (M+H), 426 (M+Na); [α]$_D^{25\ °C}$=−140.7° (c=0.17, DMSO). Anal. Calcd. for $C_{23}H_{21}N_3O_4 \cdot 0.4\ H_2O$: C, 67.27; H, 5,35; N, 10.23. Found: C, 67.28; H, 5.30; N, 10.09. The relative stereochemistry of the major product was confirmed to be the trans isomer by NOE difference experiments (DMSO-d$_6$): no NOE enhancements from the C5a proton at 1.29 ppm to the C11 proton at 6.83 ppm.

Preparation of Example 5

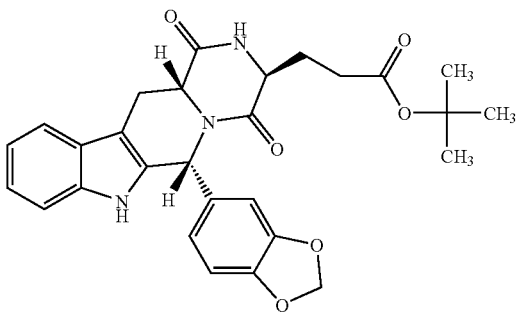

The compound of Example 5 was prepared from Compound (III) and (L)-N-Cbz-γ-tert-butyl-glutamic acid by the following synthetic scheme.

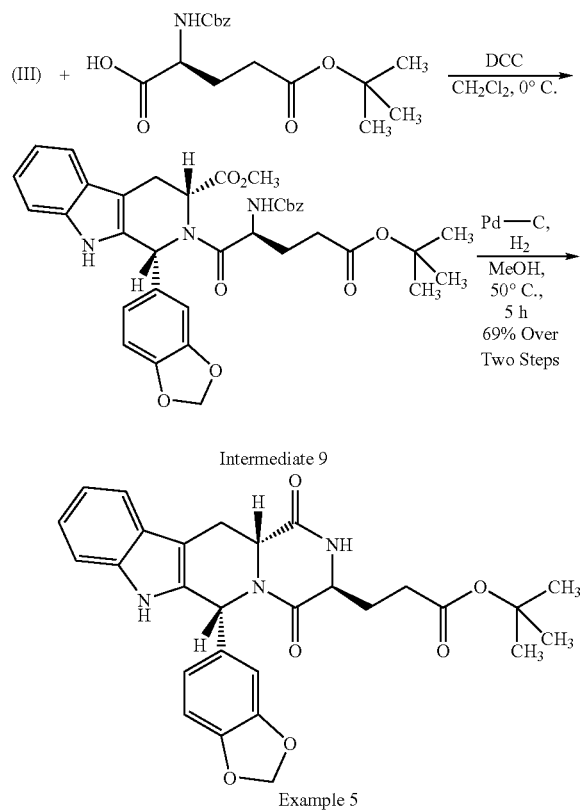

Preparation of Intermediate 9

To a solution of L-Cbz-γ-tert-butyl-glutamic acid (5.0 g, 14.8 mmol) in methylene chloride (30 mL) at 0° C. was added dicyclohexylcarbodiimide (3.09 g, 15 mmol) in one portion. The resulting white slurry was stirred at 0° C. for 30 minutes, after which Compound (III) was added. The resulting yellow slurry was slowly warmed to room temperature, and stirred for a total of 18 hours. The slurry was filtered under reduced pressure and the solid was washed with methylene chloride (5×10 mL). The filtrate was concentrated under reduced pressure and the residue was purified by flash column chromatography, eluting with methylene chloride/ethyl acetate (3:1), to provide the impure Intermediate 9 (containing a small amount of dicyclohexylcarbodiimide) as a yellow solid which was used without further purification (8.3 g): TLC $R_f$ (4:1 methylene chloride/ethyl acetate)=0.91.

Preparation of Example 5

3-((3S,6R,12aR)-6-Benzo[1,3]dioxol-5-yl-1,4-dioxo-1,2,3,4,6,7,12,12a-octahydropyrazino[1',2':1,6]-pyrido[3,4-b]indol-3-yl-propionic acid tert-butyl ester Intermediate 9 was dissolved in methanol (100 mL) and treated with a catalytic amount of 5% palladium on carbon (0.50 g, about 50% wet). The mixture was stirred under a hydrogen atmosphere at 50° C. for 6 hours, after which the palladium catalyst was removed by vacuum filtration through a plug of Celite, eluting with methanol (100 mL). The filtrate was concentrated under reduced pressure and the residue was purified by flash column chromatography, eluting with methylene chloride/ethyl acetate (4:1), to provide Example 5 as a white solid (5.1 g, 69% over two steps). A small lot of this product was further purified by recrystallization from methylene chloride at −10° C.: mp 222–227° C.; TLC $R_f$ (4:1 methylene chloride/ethyl acetate)=0.40; $^1$H NMR (300 MHz, CDCl$_3$): δ7.74 (bs, 1H), 7.65–7.56 (m, 1H), 7.30–7.10 (m, 3H), 6.90–6.83 (m, 1H), 6.75–6.67 (m, 2H), 6.26 (d, J=3.3 Hz, 1H), 5.19 (s, 1H), 5.89 (s, 1H), 5.86 (s, 1H), 4.41 (dd, J=5.7, 4.1 Hz, 1H), 4.10–4.02 (m, 1H), 3.76 (dd, J=8.0, 4.1 Hz, 1H), 3.30–3.17 (m, 1H), 2.42 (t, J=7.1 Hz, 2H), 2.28–2.00 (m, 2H), 1.44 (s, 9H); $^{13}$C NMR (125 MHz, CDCl$_3$): δ171.8, 168.7, 167.9, 147.9, 136;5, 135.6, 132.9, 126.3, 122.6, 120.6, 120.2, 118.6, 111.2, 108.3, 107.3, 106.3, 101.2, 81.2, 57.2, 55.4,.55.2, 31.3, 29.4, 28.1, 28.8 ppm; API MS m/z 504 [C$_{28}$H$_{29}$N$_3$O$_6$+H]$^+$; [α]$_D^{25°}$ c.=+31.3° (c=1.0, CHCl$_3$). Anal. Calcd. for C$_{28}$H$_{29}$N$_3$O$_8$: C, 66.79; H, 5.80; N, 8.34. Found: C, 66.27; H, 5.74; N, 8.30. The relative stereochemistry of Example 5 was confirmed to be the cis isomer by an NOE difference experiment (DMSO-d$_6$): positive NOE enhancements from the C12a proton at 4.40 ppm to the C6 proton at 6.05 ppm (1.3%) and a C12 proton at 3.45 ppm (3.3%). HPLC analysis by the previously described method showed one-major peak with a purity of 99.1%.

Preparation of Example 6

3-((3S,6R,12aR)-6-Benzo[1,3]dioxol-5-yl-1,4-dioxo-1,2,3,4,6,7,12,12a-octahydropyrazino[1',2':1,6]py-rido[3,4-b]indole-3-yl)propionic acid

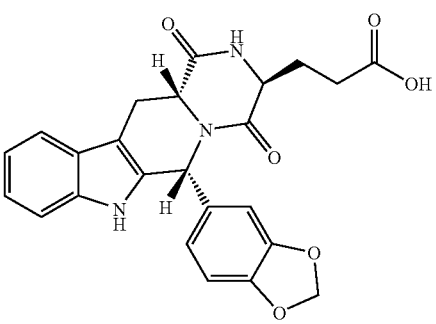

Example 6 was prepared from Example 5 by the following reaction.

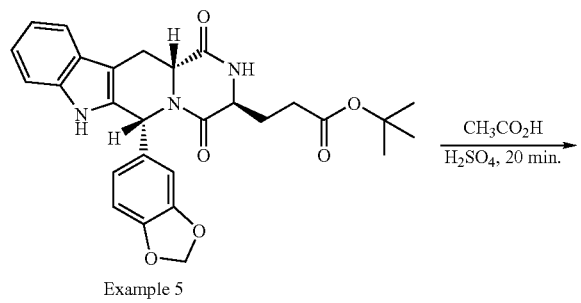

Example 5

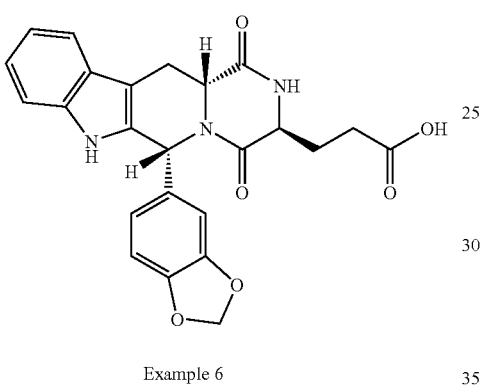

Example 6

EXAMPLE 6

To a mixture of Example 5 (1.13 g, 2.25 mmol) in acetic acid (11 mL) was added concentrated sulfuric acid (0.30 mL) dropwise. The resulting purple solution was stirred at room temperature for 30 minutes, after which water (50 mL) was added. The resulting white slurry was stirred at room temperature for 30 minutes. The solid was collected by vacuum filtration, and the solid residue was dissolved in a 70° C. mixture of acetic acid and water (2:1, 50 mL). The yellow solution then was cooled to room temperature, then additional water (50 mL) was added. The solid was collected by vacuum filtration, and dried in a vacuum oven at 70° C. overnight to yield Example 6 as a white solid (188 mg). The filtrate then was extracted with ethyl acetate to yield additional Example 6 (550 mg, total yield 74%): mp 221–231° C.; $^1$H NMR (300 MHz, DMSO-$d_6$): δ11.05 (s, 1H), 8.62 (d, J=3.8 Hz, 1H), 7.52 (d, J=7.4 Hz, 1H), 7.29 (d, J=7.4 Hz, 1H), 7.12–6.92 (m, 2H), 6.88 (s, 1H), 6.78 (s, 2H), 6.09 (s, 1H), 5.92 (s, 2H), 4.44 (dd, J=5.7, 4.4 Hz, 1H), 3.92–3.79 (m, 1H), 3.58–3.42 (m, 1H), 3.02–2.88 (m, 1H), 2.35 (t, J=7.3 Hz, 2H), 2.05–1.82 (m, 2H); $^{13}$C NMR (125 MHz, DMSO-$d_6$) δ173.7, 168.7, 167.7, 147.0, 146.0, 137.2, 136.1, 134.1, 125.7, 121.0, 119.0, 118.8, 118.0, 111.2, 108.0, 106.8, 104.5, 100.8, 55.5, 54.6, 54.3, 29.6, 28.4, 22.9 ppm; API MS m/z 448 $[C_{21}H_{20}N_4O_3$+H$]^+$; $[\alpha]_D^{25\ °C}$=+69.17° (c=0.5, DMSO). Anal. Calcd. for $C_{21}H_{20}N_4O_3 \cdot 0.75$ H$_2$O: C, 62.64; H, 4.76; N, 9.13. Found: C, 62.55; H, 4.82; N, 9.00.

Preparation of Example 7

3-((3S,6R,12aR)-6-Benzo[1,3]dioxol-5-yl-1,4-dioxo-1,2,3,4,6,7,12,12a-octahydropyrazino[1',2':1,6]pyrido[3,4-b]indol-3-yl)-propionic acid isopropyl ester

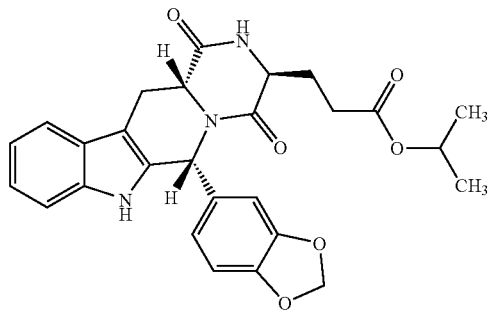

Example 7 was prepared from Example 6 by the following reaction.

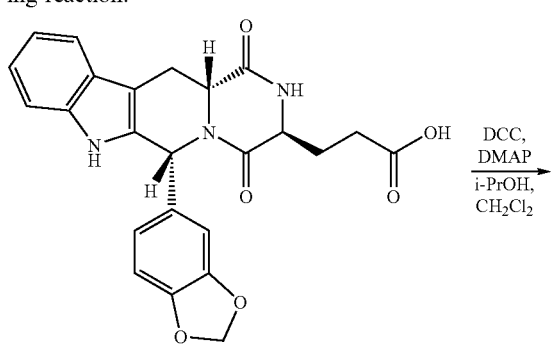

Example 6

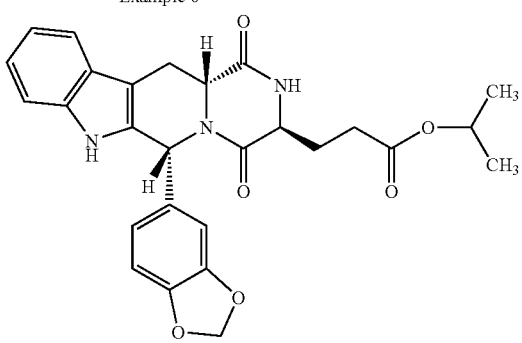

Example 7

To a solution of Example 6 (558 mg, 1.25 mmol) and 4-(dimethylamino)pyridine (DMAP, 60 mg, 0.49 mmol) in isopropanol (1.0 mL, 13.10 mmol) and methylene chloride (10 mL), at 0° C. under a nitrogen blanket, was added dicyclohexylcarbodiimide (DCC, 409 mg, 1.99 mmol) in one portion. The resulting white slurry was stirred at room temperature for 2 days. The white slurry was filtered under reduced pressure, then the solid was washed with methylene chloride (3×10 mL). The filtrate was concentrated under reduced pressure and the residue was purified by flash column chromatography, eluting with methylene chloride/ethyl acetate (4:1), to provide Example 7 (450 mg), which contained residual dicyclohexylcarbodiimide. This solid was dissolved in methylene chloride (4 mL), and the solution was stored at −10° C. overnight. The white crystals that formed were quickly filtered through a cold funnel under vacuum. The solid was washed with cold methylene chloride (2×1 mL), then dried in a vacuum oven at 60° C. for 24 hours to provide Example 7 as a white solid (186 mg, 30%): TLC $R_f$ (4:1 methylene chloride/ethyl acetate)=0.31; $^1$H NMR (300 MHz, DMSO-$d_6$): δ11.05 (s, 1H), 8.60 (d, J=3.7 Hz, 1H), 7.53 (d, J=7.4 Hz, 1H), 7.30 (d, J=7.4 Hz, 1H), 7.12–6.93 (m, 2H), 6.87 (s, 1H), 6.78 (s, 2H), 6.09 (s, 1H), 5.92 (s, 2H), 4.87 (sep, J=6.2 Hz, 1H), 4.44 (dd, J=5.7, 4.4 Hz, 1H), 3.90–3.79 (m, 1H), 3.55–3.47 (m, 1H), 3.02–2.87 (m, 1H), 2.45–2.30 (m, 2H), 2.03–1.87 (m, 2H), 1.22–1.05 (m, 6H); $^{13}$C NMR (125 MHz, DMSO-$d_6$): δ171.6, 168.5, 167.7, 147.0, 146.0, 137.2, 136.1, 134.1, 125.7, 121.1, 119.0, 118.8, 118.0, 111.2, 108.0, 106.8, 104.5, 100.8, 67.1, 55.6, 54.6, 54.3, 29.8, 28.4, 22.9, 21.6 ppm; API MS m/z 491 $[C_{27}H_{27}N_3O_6+H]^+$; $[\alpha]_D^{25°\ C.}$=+47.3° (c=0.5, CHCl$_3$). Anal. Calcd. for $C_{27}H_{27}N_3O_6$: C, 66.25; H, 5.56; N, 8.58. Found: C, 65.85; H, 5.63; N, 8.54. The stereochemistry was confirmed to be the cis isomer by an NOE difference experiment: positive NOE enhancements from the C12a proton at 4.44 ppm to the C6 proton at 6.09 ppm (1.8%) and a C12 proton at 3.50 ppm (2.7%).

Preparation of Example 8

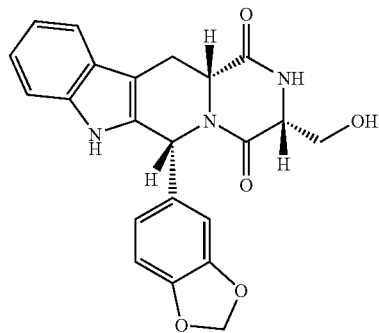

The compound of Example 8 was prepared from Compound (III) and N-Cbz-(R)-(+)-oxazolidinecarboxylic acid as depicted in the following synthetic sequence.

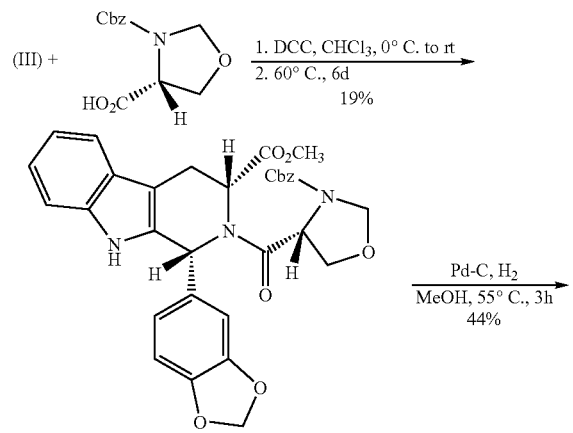

Intermediate 10

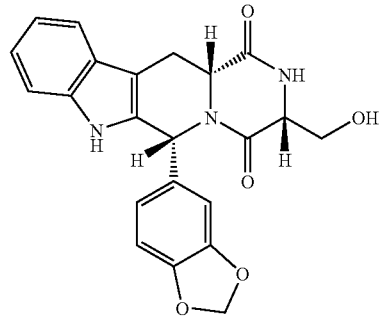

Example 8

Preparation of Intermediate 10

To a solution of Cbz-(R)-(+)-oxazolidine-carboxylic acid (1.3 g, 5.1 mmol) in chloroform (20 mL), at 0° C., was added dicyclohexylcarbodiimide (1.1 g, 5.3 mmol) in one portion. The resulting white slurry was stirred at 0° C. for 30 minutes, after which Compound (III) (1.7 g, 5.0 mmol) was added to the mixture. The resulting yellow slurry was warmed to room temperature, after which the slurry was heated at 60° C. for 6 days. The solution then was cooled to room temperature, concentrated under reduced pressure to one-third of the slurry volume, and the resulting solid removed by vacuum filtration. The filtrate was concentrated under reduced pressure, and the residue was purified by flash column chromatography, eluting with methylene chloride/acetone (1:0 to 32:1), to provide Intermediate 10 as a colorless solid (0.56 g, 19%): TLC $R_f$ (32:1 methylene chloride/acetone)=0.34.

Preparation of Example 8

(3R,6R,12aR)-6-Benzo[1,3]dioxo-5-yl-3-hydroxymethyl-2,3,6,7,12,12a-hexahydropyrazino[1',2':1,;6]pyrido[3,4-b]indole-1,4-dione Intermediate 9 (0.55 g, 0.95 mmol) in methanol (50 mL) and acetic acid (15 mL) was treated with a catalytic amount of 10% palladium on carbon (0.08 g, about 10% wet). The mixture was stirred under a hydrogen atmosphere at 55° C. for 3 hours, after which the palladium catalyst was removed by vacuum filtration through a plug of Celite, eluting with methanol. The filtrate was concentrated under reduced pressure to provide a yellow oil which was purified by flash column chromatography, eluting with methylene chloride/ethyl acetate/methanol (9:1:0.5), to yield Example 8 as a white foamy solid (0.17 g, 44%): mp 194–200° C.; TLC $R_f$ (8:1:0.5 methylene chloride/ethyl acetate/methanol)=0.43; $^1$H NMR (300 MHz, CDCl$_3$): δ7.87 (s, 1H), 7.58 (d, J=6.6 Hz, 1H), 7.29–7.25 (m, 2H), 7.20–7.12 (m, 2H), 6.82 (m, 1H), 6.73–6.64 (m, 3H), 6.16 (s, 1H), 5.86 (d, J=5.7 Hz, 2H), 4.39–4.33 (m, 1H), 4.15–4.12 (m, 1H), 4.02–3.90 (m, 2H), 3.75–3.69 (m, 1H), 3.28–3.19 (m, 1H); $^{13}$C NMR (75 MHz, CDCl$_3$): δ168.7, 148.6, 147.3, 136.7, 135.6, 132.9, 126.5, 122.8, 120.4, 120.1, 118.8, 111.4, 108.6, 107.1, 106.4, 101.3, 62.9, 56.9, 56.4, 55.6, 23.3 ppm; CI MS (methane) m/z 406 $[C_{22}H_{19}N_3O_5+H]^+$; $[\alpha]_D^{25°\ C.}$=+58.7 (c=0.15, methanol). Anal. Calcd. for $C_{23}H_{19}N_3O_5 \cdot 0.75$ $H_2O$: C, 63.08; H, 4.93; N, 10.03. Found: C, 63.17; H, 4.90; N, 9.79.

Preparation of Example 9
The compound of Example 9 can be prepared by the following synthetic sequence.
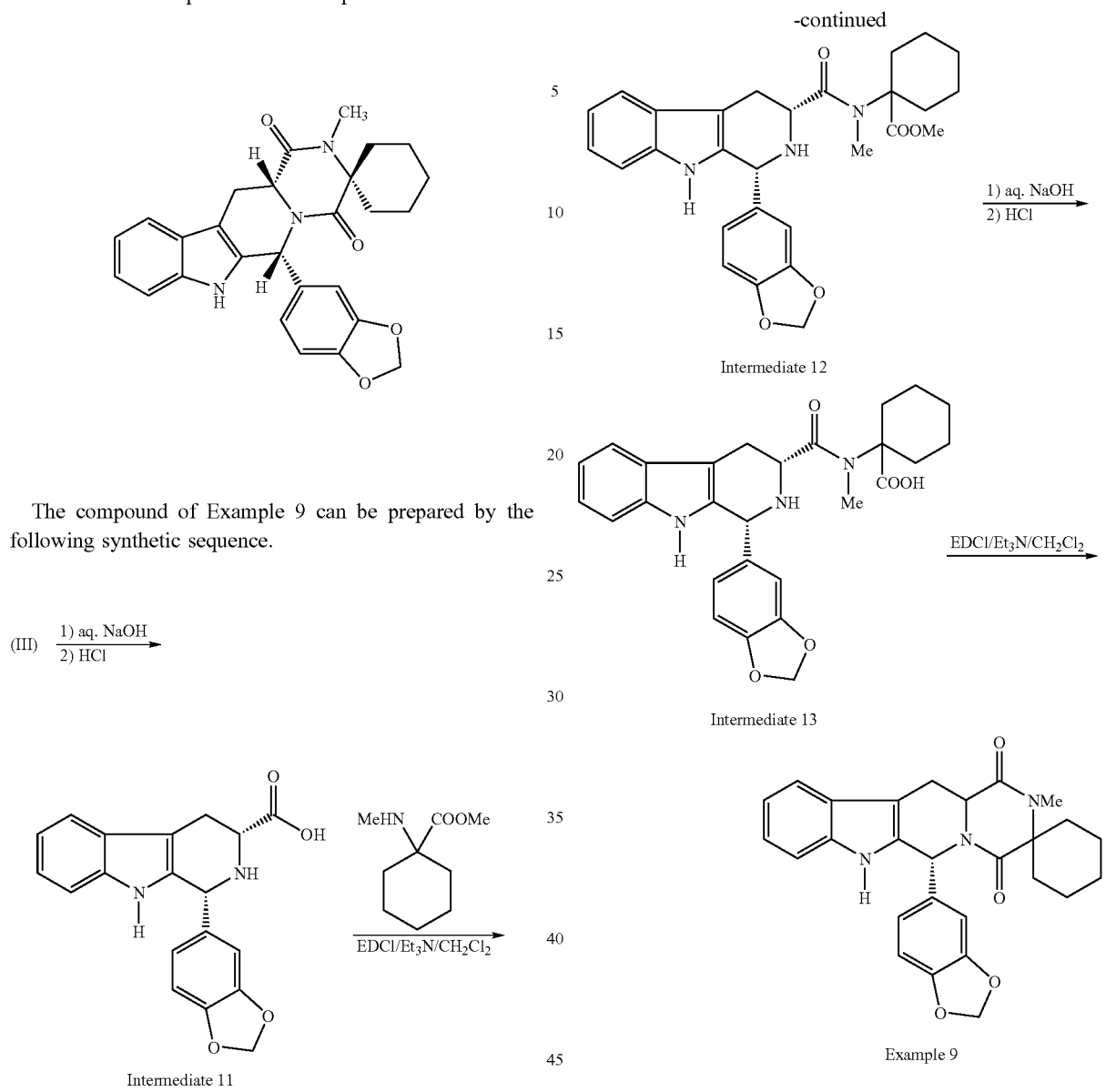
The following Examples 10–37 were prepared by methods analogous to Examples 1–9.
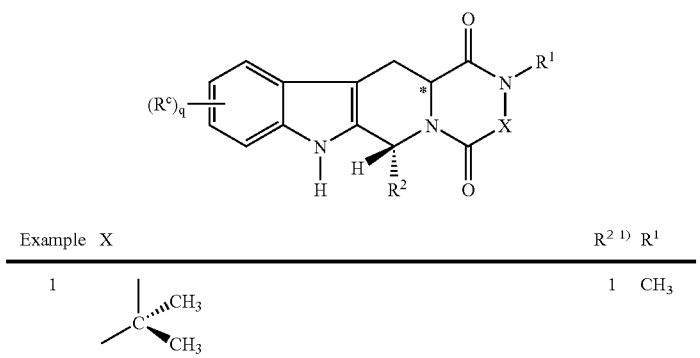
| Example | X | R[2] [1)] | R[1] |
|---|---|---|---|
| 1 | —C(CH₃)₂— | | CH₃ |

-continued
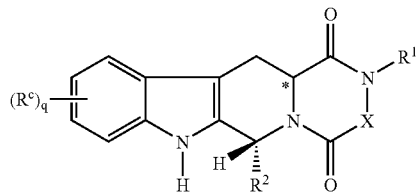
| Example | X | R² ¹⁾ | R¹ |
|---|---|---|---|
| 2 | | 1 | H |
| 3 | >N−H | 1 | H |
| 4 | −CH₂−CH₂− | 1 | CH₃ |
| 5 | >C(H)−(CH₂)₂C(=O)OC(CH₃)₃ | 1 | H |
| 6 | >C(H)−(CH₂)₂C(=O)OH | 1 | H |
| 7 | >C(H)−(CH₂)₂C(=O)CH(CH₃)₂ | 1 | H |
| 8 | >C(H)−CH₂OH | 1 | H |
| 9 | cyclohexyl | 1 | CH₃ |
| 10 | >N−CH₃, | 1 | CH₃ |
| 11 | >C(H)−(CH₂)₂-tetrazolyl | 1 | H |
| 12 | >C(H)−(CH₂)₄NH₂ | 1 | H |
| 13 | >C(H)−(CH₂)₂SO₂NH₂ | 1 | H |

-continued
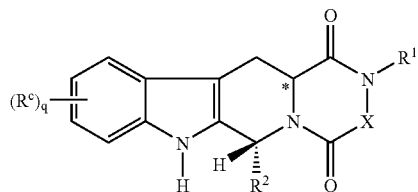
| Example | X | R² ¹⁾ | R¹ |
|---|---|---|---|
| 14 | —C(H)(CH₃)—(CH₂)₅C(=O)OH | 1 | CH₃ |
| 15 | —C(H)(CH₃)—(CH₂)C(=O)OC(CH₃)₃ | 1 | H |
| 16 | —C(H)(CH₃)—CH₂OCH₂—C₆H₅ | 1 | H |
| 17 | —C(H)(CH₃)—CH₂—C₆H₄—C(=O)OH | 1 | CH₃ |
| 18 | —C(H)(CH₃)—CH₂C(=O)OH | 1 | H |
| 19 | —C(H)(CH₃)—CH₂C(=O)OH | 1 | H |
| 20 | —C(H)(CH₃)—CH₂—(N-pyrazolyl) | 1 | H |
| 21 | —C(H)(CH₃)—(CH₂)₂NH₂ | 1 | H |
| 22 | —C(H)(CH₃)—CH₂NH₂ | 1 | H |
| 23 | —C(H)(CH₃)—CH₂Cl | 1 | H |
| 24 | —C(H)(CH₃)—CH₂C(=O)NHCH₂—C₆H₄—N(CH₃)₂ | 1 | H |
| 25 | —C(H)(CH₃)—CH₂C(=O)—N(piperazinyl)N—CH₃ | 1 | H |

-continued
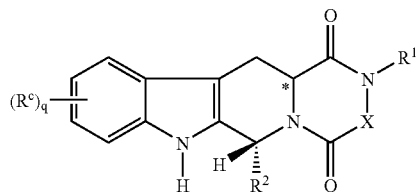
| Example | X | R² ¹⁾ | R¹ |
|---|---|---|---|
| 26 | —C(H)(CH₃)—CH₂C(=O)NH(CH₂)₂—N(pyrrolidine) | 1 | H |
| 27 | —C(H)(CH₃)—CH₂—(3-pyridyl) | 1 | H |
| 28 | —C(H)(CH₃)—CH₂C(=O)OCH₃ | 1 | H |
| 29 | —C(H)(CH₃)—CH₂C(=O)O(CH₂)₆CH₃ | 1 | H |
| 30 | —C(H)(CH₃)—CH₂C(=O)OCH₂CH₃ | 1 | H |
| 31 | —C(H)(CH₃)—CH₂C(=O)OCH(CH₃)₂ | 1 | H |
| 32 | —C(H)(CH₃)—CH₂C(=O)O-cyclopentyl | 1 | H |
| 33 | —C(H)(CH₃)—CH₂C(=O)OCH₂CF₃ | 1 | H |
| 34 | —C(H)(CH₃)—(CH₂)₂C(=O)OC(CH₃)₃ | 1 | H |
| 35 | —C(H)(CH₃)—CH₂C(=O)C(CH₃)₃ | 1 | H |
| 36 | —C(H)(CH₃)—(CH₂)₂C(=O)OH | 1 | H |
| 37 | —C(H)(CH₃)—(CH₂)₂C(=O)OCH₂CH₃ | 1 | H | for $R^2$, the designation 1 is

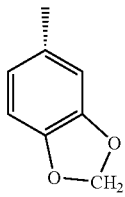

and the designation 2 is

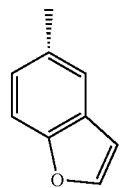

Compounds of the present invention can be formulated into tablets for oral administration. For example, a compound of formula (I) can be formed into a dispersion with a polymeric carrier by the coprecipitation method set forth in WO 96/38131, incorporated herein by reference. The coprecipitated dispersion then can be blended with excipients, then pressed into tablets, which optionally are film-coated.

The compounds of structural formula (I) were tested for an ability to inhibit PDE5. The ability of a compound to inhibit PDE5 activity is related to the $IC_{50}$ value for the compound, i.e., the concentration of inhibitor required for 50% inhibition of enzyme activity. The $IC_{50}$ value for compounds of structural formula (I) were determined using recombinant human PDE5.

The compounds of the present invention typically exhibit an $IC_{50}$ value against recombinant human PDE5 of less than about 50 μM, and preferably less than about 25 μM, and more-preferably less than about 15 μm. The compounds of the present invention typically exhibit an $IC_{50}$ value against recombinant human PDE5 of less than about 1 μM, and often less than about 0.05 μM. To achieve the full advantage of the present invention, a present PDE5 inhibitor has an $IC_{50}$ of about 0.1 nM to about 15 μM.

The production of recombinant human PDEs and the $IC_{50}$ determinations can be accomplished by well-known methods in the art. Exemplary methods are described as follows:

Expression of Human PDEs

Expression in *Saccharomyces Cerevisiae* (Yeast)

Recombinant production of human PDE1B, PDE2, PDE4A, PDE4B, PDE4C, PDE4D, PDE5, and PDE7 was carried out similarly to that described in Example 7 of U.S. Pat. No. 5,702,936, incorporated herein by reference, except that the yeast transformation vector employed, which is derived from the basic ADH2 plasmid described in Price et al., *Methods in Enzymology*, 185, pp. 308–318 (1990), incorporated yeast ADH2 promoter and terminator sequences and the *Saccharomyces cerevisiae* host was the protease-deficient strain BJ2-54 deposited on Aug. 31, 1998 with the American Type Culture Collection, Marassas, Va., under accession number ATCC 74465. Transformed host cells were grown in 2× SC-leu medium, pH 6.2, with trace metals, and vitamins. After 24 hours, YEP-medium-containing glycerol was added to a final concentration of 2× YET/3% glycerol. Approximately 24 hr later, cells were harvested, washed, and stored at −70° C.

Human Phosphodiesterase Preparations

Phosphodiesterase Activity Determinations

Phosphodiesterase activity of the preparations was determined as follows. PDE assays utilizing a charcoal separation technique were performed essentially as described in Loughney et al. (1996). In this assay, PDE activity converts [32P]cAMP or [32P]cGMP to the corresponding [32P]5'-AMP or [32P]5'-GMP in proportion to the amount of PDE activity present. The [32P]5'-AMP or [32P]5'-GMP then was quantitatively converted to free [32P]phosphate and unlabeled adenosine or guanosine by the action of snake venom 5'-nucleotidase. Hence, the amount of [32P]phosphate liberated is proportional to enzyme activity. The assay was performed at 30° C. in a 100 μL reaction mixture containing (final concentrations) 40 mM Tris HCl (pH 8.0), 1 μM $ZnSO_4$, 5 mM $MgCl_2$, and 0.1 mg/mL bovine serum albumin (BSA). PDE enzyme was present in quantities that yield <30% total hydrolysis of substrate (linear assay conditions). The assay was initiated by addition of substrate (1 mM [32P]cAMP or cGMP), and the mixture was incubated for 12 minutes. Seventy-five (75) μg of Crotalus atrox venom then was added, and the incubation was continued for 3 minutes (15 minutes total). The reaction was stopped by addition of 200 μL of activated charcoal (25 mg/mL suspension in 0.1 M $NaH_2PO_4$, pH 4). After centrifugation (750×g for 3 minutes) to sediment the charcoal, a sample of the supernatant was taken for radioactivity determination in a scintillation counter and the PDE activity was calculated.

Purification of PDE5 From *S. cerevisiae*

Cell pellets (29 g) were thawed on ice with an equal volume of Lysis Buffer (25 mM Tris HCl, pH 8, 5 mM $MgCl_2$, 0.25 mM DTT, 1 mM benzamidine, and 10 μM $ZnSO_4$). Cells were lysed in a Microfluidizer® (Microfluidics Corp.) using nitrogen at 20,000 psi. The lysate was centrifuged and filtered through 0.45 μm disposable filters. The filtrate was applied to a 150 mL column of Q SEPHAROSE® FastFlow (Pharmacia). The column was washed with 1.5 volumes of Buffer A (20 mM Bis-Tris Propane, pH 6.8, 1 mM $MgCl_2$, 0.25 mM DTT, 10 μM $ZnSO_4$) and eluted with a step gradient of 125 mM NaCl in Buffer A followed by a linear gradient of 125–1000 mM NaCl in Buffer A. Active fractions from the linear gradient were applied to a 180 mL hydroxyapatite column in Buffer B (20 mM Bis-Tris Propane (pH 6.8), 1 mM $MgCl_2$, 0.25 mM DTT, 10 μM $ZnSO_4$, and 250 mM KCl). After loading, the column was washed with 2 volumes of Buffer B and eluted with a linear gradient of 0–125 mM potassium phosphate in Buffer B. Active fractions were pooled, precipitated with 60% ammonium sulfate, and resuspended in Buffer C (20 mM Bis-Tris Propane, pH 6.8 , 125 mM NaCl, 0.5 mM DTT, and 10 μM $ZnSO_4$). The pool was applied to a 140 mL column of SEPHACRYL® S-300 HR and eluted with Buffer C. Active fractions were diluted to 50% glycerol and stored at −20° C.

The resultant preparations were about 85% pure by SDS-PAGE. These preparations had specific activities of about 3 μmol cGMP hydrolyzed per minute per milligram protein.

Inhibitory Effect on cGMP-PDE cGMP-PDE activity of compounds of the present invention was measured using a one-step assay adapted from Wells et al., *Biochim. Biophys. Acta,* 384, 430 (1975). The reaction medium contained 50 mM Tris-HCl, pH 7.5, 5 mM magnesium acetate, 250 μg/ml 5'-Nucleotidase, 1 mM EGTA, and 0.15 μM 8-[$H^3$]-cGMP. Unless otherwise indicated, the enzyme used was a human recombinant PDE5 (ICOS Corp., Bothell, Wash.).

Compounds of the invention were dissolved in DMSO finally present at 2% in the assay. The incubation time was 30 minutes during which the total substrate conversion did not exceed 30%.

The $IC_{50}$ values for the compounds examined were determined from concentration-response curves typically using concentrations ranging from 10 nM to 10 μM. Tests against other PDE enzymes using standard methodology showed that compounds of the invention are selective for the cGMP-specific PDE enzyme.

Biological Data

The compounds according to the present invention were typically found to exhibit an $IC_{50}$ value of less than 500 nM (i.e., 0.5 μm). An in vitro test data for representative compounds of the invention is given in the following table

TABLE 1

In vitro Results

| Example | PDE5 $IC_{50}$ (nM) |
|---|---|
| 1 | 161.0 |
| 2 | 2.2 |
| 3 | 113.0 |
| 4 | 593.0 |
| 5 | 0.6 |
| 6 | 1.0 |
| 7 | 0.2 |
| 8 | 28.0 |
| 12 | 0.03 |
| 15 | 8.6 |
| 16 | 9.5 |
| 18 | 9.2 |
| 19 | 20 |
| 20 | 600 |
| 21 | 420 |
| 22 | 80 |
| 23 | 10 |
| 24 | 90 |
| 25 | 80 |
| 26 | 50 |
| 27 | 90 |
| 28 | 10 |
| 29 | 30 |
| 30 | 8.6 |
| 31 | 7.8 |
| 32 | 7.0 |
| 33 | 9.0 |
| 34 | 7.5 |
| 35 | 20 |
| 36 | 7.7 |
| 37 | 8.0 |

Obviously, many modifications and variations of the invention as hereinbefore set forth can be made without departing from the spirit and scope thereof, and, therefore, only such limitations should be imposed as are indicated by the appended claims.

What is claimed is:

1. A compound having a formula

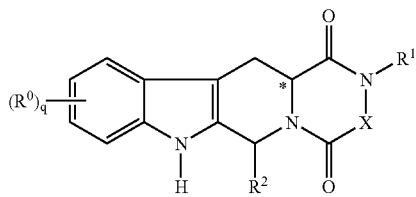

wherein $R^o$, independently, is selected from the group consisting of halo and $C_{1-6}$alkyl;
$R^1$ is selected from the group consisting of hydrogen, $C_{1-6}$alkyl, $C_{2-6}$alkenyl, $C_{2-6}$alkynyl, halo$C_{1-6}$alkyl, $C_{3-8}$cycloalkyl, $C_{3-8}$cycloalkyl$C_{1-3}$alkyl, aryl$C_{1-3}$alkyl, and heteroaryl$C_{1-3}$alkyl;
$R^2$ is selected from the group consisting of substituted benzene, an optionally substituted monocyclic aromatic ring selected from the group consisting of thiophene, furan, and pyridine, and an optionally substituted bicyclic ring

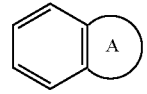

wherein the fused ring A is a 5- or 6-membered ring, saturated or partially or fully unsaturated, and comprises carbon atoms and optionally one or two heteroatoms selected from oxygen, sulfur, and nitrogen;
X is $CR^3R^4$;
$R^3$ is selected from the group consisting of hydrogen and $C_{1-3}$alkyl;
$R^4$ is selected from the group consisting of halo$C_{1-4}$alkyl, aryl, heteroaryl, Het, $C_{3-8}$cycloalkyl, $OR^a$, $C(=O)OR^a$, $C(=O)R^a$, $C(=O)NR^aSO_2R^b$, $C(=O)NR^aR^b$, $C(=S)NR^aR^b$, $C_{1-6}$alkyleneC(=O)$OR^a$, $C_{1-4}$alkyleneC(=O)$NR^aR^b$, $C_{1-4}$alkyleneNR^aR^b$, $C_{1-4}$alkyleneOR^a$, $C_{1-4}$alkyleneSO$_2$NR^aR^b$, $C_{1-4}$alkyleneheteroaryl, $C_{1-4}$alkyleneHet, $C_{1-4}$alkyleneC(=O)$C_{1-4}$alkyleneHet, $C_{1-4}$alkyleneC(=O)Het, $C_{1-4}$alkyleneC(=O)$OR^a$, $C(=O)C_{1-4}$alkyleneHet, $C(=O)NR^a$alkyleneOR$^b$, $C(=O)NR^aC_{1-4}$alkyleneHet, $NR^aC_{1-4}$alkyleneNR^aR^b$, $NR^aC(=O)R^b$, $NR^aC(=O)NR^aR^b$, $N(SO_2C_{1-4}$alkyl)$_2$, and $NR^a(SO_2C_{1-4}$alkyl), with the proviso that when $R^3$ is hydrogen, $R^4$ is different from aryl;
or $R^3$ and $R^4$ together represent a 4- to 6-membered alkyl or alkenyl chain component of a 5- to 7-membered ring;
$R^a$ and $R^b$, independently, are selected from the group consisting of hydrogen, $C_{1-8}$alkyl, aryl, heteroaryl, halo$C_{1-6}$alkyl, $C_{1-4}$alkyleneHet, aryl$C_{1-3}$alkyl, heteroaryl$C_{1-3}$alkyl, $C_{1-4}$alkylenearyl, $C_{3-8}$cycloalkyl, $C_{1-3}$alkyleneheteroaryl, and Het;
Het is a 4- to 7-membered heterocyclic group, saturated or partially unsaturated, containing at least one heteroatom selected from the group consisting of oxygen, nitrogen, and sulfur, and optionally substituted with one or more $C_{1-6}$alkyl, $NR^aR^b$, and $C(=O)OR^a$;
q is 0, 1, 2, 3, or 4;
or a pharmaceutically acceptable salt or hydrate thereof.

2. The compound of claim 1 represented by the formula

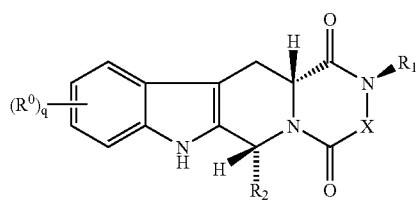

or a pharmaceutically acceptable salt or hydrate thereof.

3. The compound of claim 1 wherein $R^4$ is selected from the group consisting of, $C_{1-6}$alkyleneC(=O)OR$^a$, C(=O)OR$^a$, C(=S)NR$^a$R$^b$, $C_{5-7}$spiro when combined with $R^3$, $C_{1-4}$alkyleneC(=O)NR$^a$R$^b$, $C_{1-4}$alkyleneNR$^a$R$^b$, $C_{1-4}$alkyleneOR$^a$, $C_{1-4}$alkyleneSO$_2$NR$^a$R$^b$, $C_{1-4}$alkyleneheteroaryl, haloC$_{1-4}$alkyl, $C_{1-4}$alkyleneHet, and $C_{1-4}$alkyleneC(=O)C$_{1-4}$alkyleneHet;

and $R^a$ and $R^b$, independently, are selected from the group consisting of $C_{1-8}$alkyl, hydrogen, $C_{1-4}$alkylenearyl, Het, $C^{1-4}$alkyleneHet, $C_{3-8}$cycloalkyl, and haloC$_{1-6}$alkyl.

4. The compound of claim 3 wherein Het, aryl, and heteroaryl are optionally substituted with one or more of C(=O)OR$^a$, and $C_{1-6}$alkyl.

5. The compound of claim 1 wherein $R^3$ is selected from the group consisting of hydrogen and methyl.

6. The compound of claim 1 wherein $R^4$ is selected from the group consisting of $C_{1-4}$alkyleneC(=O)NH$_2$, $C_{1-4}$alkyleneNH$_2$, $C_{1-4}$alkyleneC(=O)OC$_{1-7}$alkyl, $C_{1-6}$alkyleneC(=O)OR$^a$, $C_{1-3}$alkyleneOH, $C_{1-4}$alkyleneSO$_2$NH$_2$, $C_{1-4}$alkyleneOC$_{1-3}$alkylenearyl, haloC$_{1-3}$alkyl, $C_{1-3}$alkylenearyl, $C_{1-4}$alkyleneC(=O)OC$_{1-3}$haloalkyl,

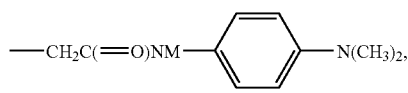

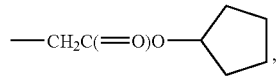

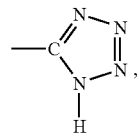

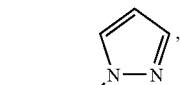

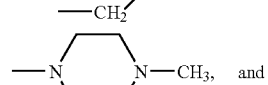

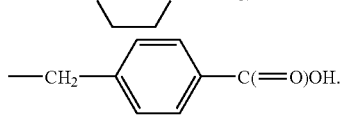

7. The compound of claim 1 wherein $R^3$ and $R^4$ are taken together to form a 5- or 6-membered spiro group.

8. The compound of claim 1 wherein $R^2$ is

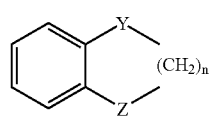

wherein n is an integer 1 or 2, and Y and Z, independently, are CH$_2$, O, S, or NR$^a$.

9. The compound of claim 1 wherein $R^2$, substituted or unsubstituted, is selected from the group consisting of

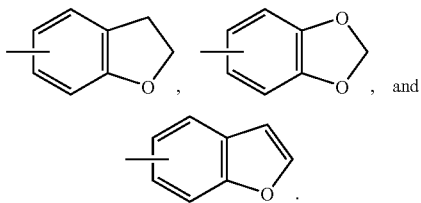

10. A compound of claim 1 selected from the group consisting of

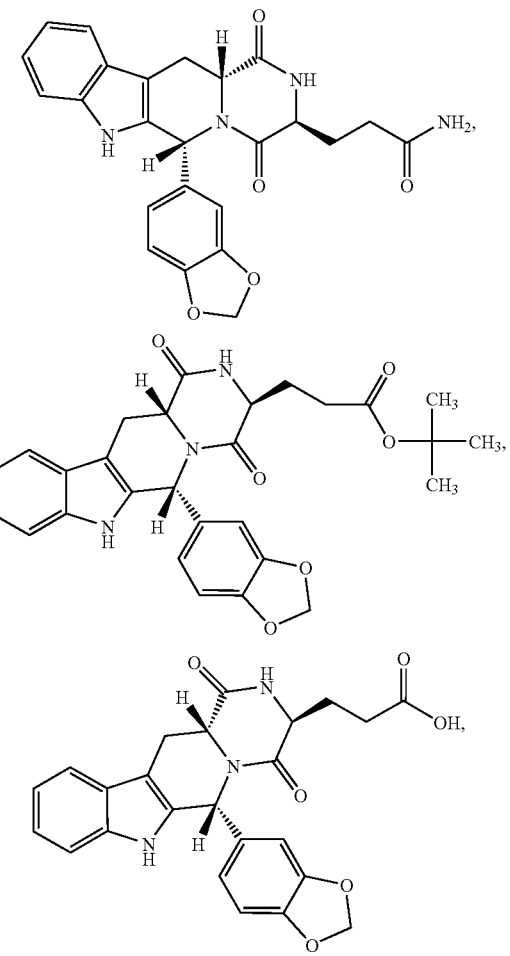

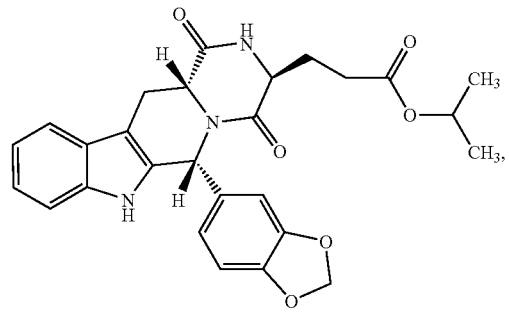

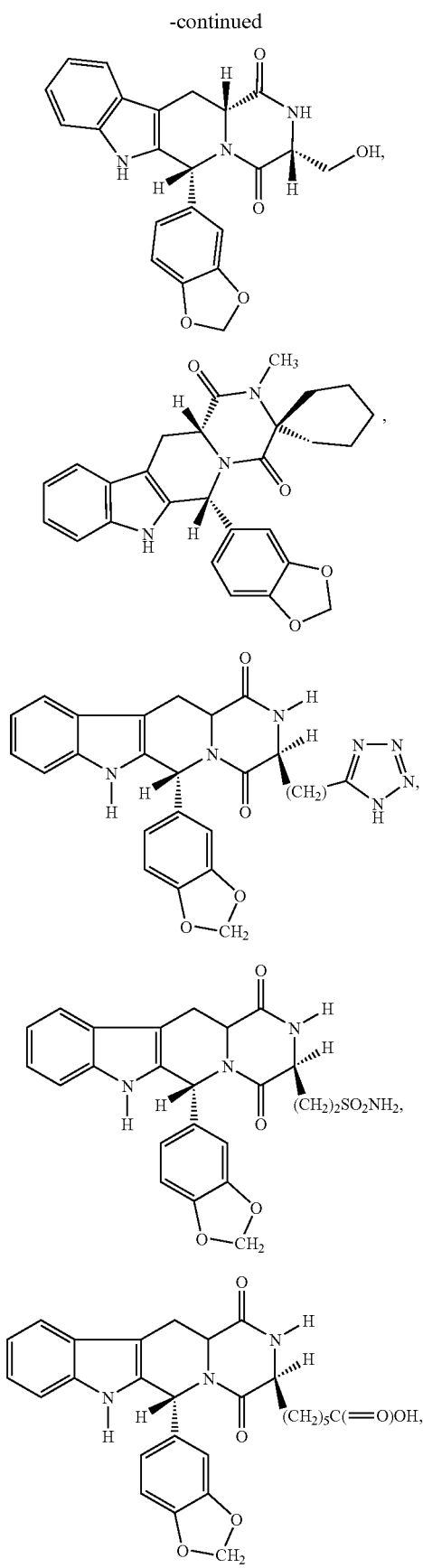
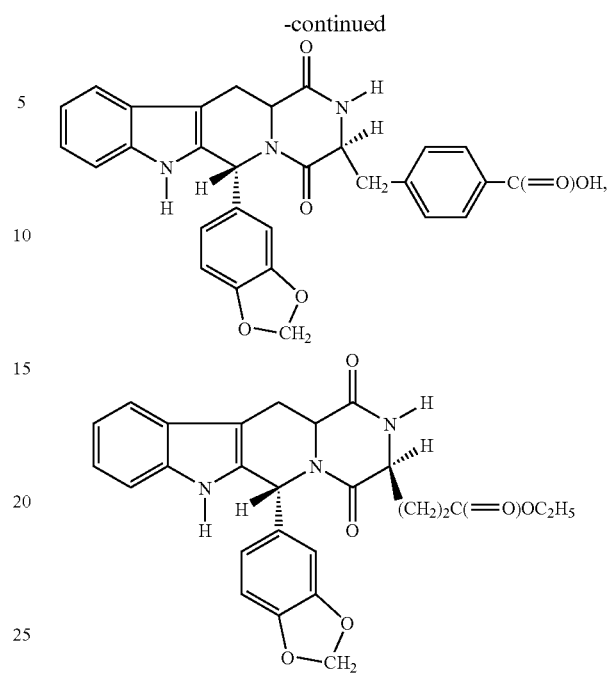

or a pharmaceutically acceptable salt or hydrate thereof.

11. A compound of claim 1 selected from the group consisting of
- (3S,6R,12aR)-3-(4-aminobutyl)-6-benzo[1,3]-dioxol-5-yl-2,3,6,7,12,12a-hexahydropyrazino-[1',2':1,6]pyrido[3,4-b]indole-1,4-dione,
- ((3S,6R,12aR)-6-benzo[1,3]dioxol-5-yl-1,4-dioxo-1,2,3,4,6,7,12,12a-octahydropyrazino[1',2':1,6]-pyrido[3,4-b]indol-3-yl)acetic acid tert-butyl ester,
- (3S,6R,12aR)-6-benzo[1,3]dioxol-5-yl-3-benzyloxymethyl-2,3,6,7,12,12a-hexahydropyrazino-[1',2':1,6]pyrido[3,4-b]indole-1,4-dione,
- ((3S,6R,12aR)-6-benzo[1,3]dioxol-5-yl-1,4-dioxo-1,2,3,4,6,7,12,12a-octahydropyrazino[1',2':1,6]-pyrido[3,4-b]indol-3-yl)acetic acid,
- ((3R,6R,12aR)-6-benzo[1,3]dioxol-5-yl-1,4-dioxo-1,2,3,4,6,7,12,12a-octahydropyrazino[1', 2':1,6]-pyrido[3,4-b]indol-3-yl)acetic acid,
- (6R,12aR)-6-benzo[1,3]dioxol-5-yl-3-pyrazol-1-ylmethyl-2,3,6,7,12,12a-hexahydropyrazino[1',2':1,6]-pyrido[3,4-b]indole-1,4-dione,
- (3S,6R,12aR)-3-(2-aminoethyl)-6-benzo[1,3]-dioxol-5-yl-2,3,6,7,12, 12a-hexahydropyrazino[1',2':1,6]pyrido[3,4-b]indole-1,4-dione,
- (3S,6R,12aR)-3-aminomethyl-6-benzo[1,3]dioxol-5-yl-2,3,6,7,12,12a-hexahydropyrazino[1',2':1,6]-pyrido[3,4-b]indole-1,4-dione,
- (3R,6R,12aR)-6-benzo[1,3]dioxol-5-yl-3-chloromethyl-2,3,6,7,12,12a-hexahydropyrazino-[1',2':1,6]pyrido[3,4-b]indole-1,4-dione,
- 2-((3S,6R,12aR)-6-benzo[1,3]dioxol-5-yl-1,4-dioxo-1,2,3,4,6,7,12,12a-octahydropyrazino[1',2':1,6]-pyrido[3,4-b]indol-3-yl)-N-(4-dimethylaminobenzyl)-acetamide,
- 3S,6R,12aR)-6-benzo[1,3]dioxol-5-yl-3-[2-(4-methyl-piperazin-1-yl)-2-oxo-ethyl]-1,2,3,6,7,12,12a-hexahydropyrazino[1',2':1,6]pyrido[3,4-b]indole-1,4-dione, 2-((6R,12aR)-6-benzo[1,3]dioxol-5-yl-1,4-dioxo-1,2,3,4,
6,7,12,12a-oxtahydropyrazino[1',2':1,6]-pyrido[3,4-b]
indol-3-yl)-N-(2-pyrrolidin-1-yl-ethyl)-acetamide,
(3S,6R,12aR)-6-benzo[1,3]dioxol-5-yl-3-pyridin-3-ylmethyl-2,3,6,7,12,12a-hexahydropyrazino-[1',2':1,6]pyrido[3,4-b]indole-1,4-dione,
((3S,6R,12aR)-6-benzo[1,3]dioxol-5-yl-1,4-dioxo-1,2,3,4,6,7,12,12a-octahydropyrazino[1',2':1,6]-pyrido[3,4-b]indol-3-yl)acetic acid methyl ester,
((3S,6R,12aR)-6-benzo[1,3]dioxol-5-yl-1,4-dioxo-1,2,3,4,6,7,12,12a-octahydropyrazino[1',2':1,6]-pyrido[3,4-b]indol-3-yl)acetic acid heptyl ester,
((3S,6R,12aR)-6-benzo[1,3]dioxol-5-yl-1,4-dioxo-1,2,3,4,6,7,12,12a-octahydropyrazino[1',2':1,6]-pyrido[3,4-b]indol-3-yl)acetic Acid ethyl ester,
((3S,6R,12aR)-6-benzo[1,3]dioxol-5-yl-1,4-dioxo-1,2,3,4,6,7,12,12a-octahydropyrazino[1',2':1,6]-pyrido[3,4-b]indol-3-yl)acetic acid isopropyl ester,
((3S,6R,12aR)-6-benzo[1,3]dioxol-5-yl-1,4-dioxo-1,2,3,4,6,7,12,12a-octahydropyrazino[1',2':1,6]-pyrido[3,4-b]indol-3-yl)acetic acid cyclopentyl ester,
((3S,6R,12aR)-6-benzo[1,3]dioxol-5-yl-1,4-dioxo-1,2,3,4,6,7,12,12a-octahydropyrazino[1',2':1,6]-pyrido[3,4-b]indol-3-yl)acetic acid 2,2,2-trifluoroethyl ester,
3-((3S,6R,12aR)-6-benzofuran-5-yl-1,4-dioxo-1,2,3,4,6,7,12,12a-octahydropyrazino[1',2':1,6]-pyrido[3,4-b]indol-3-yl)propionic acid tert-butyl ester,
((3S,6R,12aR)-6-benzofuran-5-yl-1,4-dioxo-1,2,3,4,6,7,12,12a-octahydropyrazino[1',2':1,6]-pyrido[3,4-b]indol-3-yl)acetic acid tert-butyl ester,
3-((3S,6R,12aR)-6-benzo[1,3]dioxol-5-yl-1,4-dioxo-1,2,3,4,6,7,12,12a-octahydropyrazino[1',2':1,6]-pyrido[3,4-b]indol-3-yl)propionic acid ethyl ester, or a pharmaceutically acceptable salt or hydrate thereof.

12. A compound having a formula

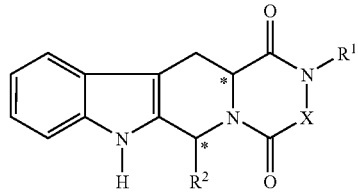

wherein $R^1$ is hydrogen or methyl, $R^2$ is

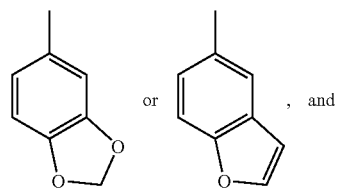, and

X is selected from the group consisting of

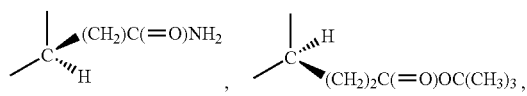

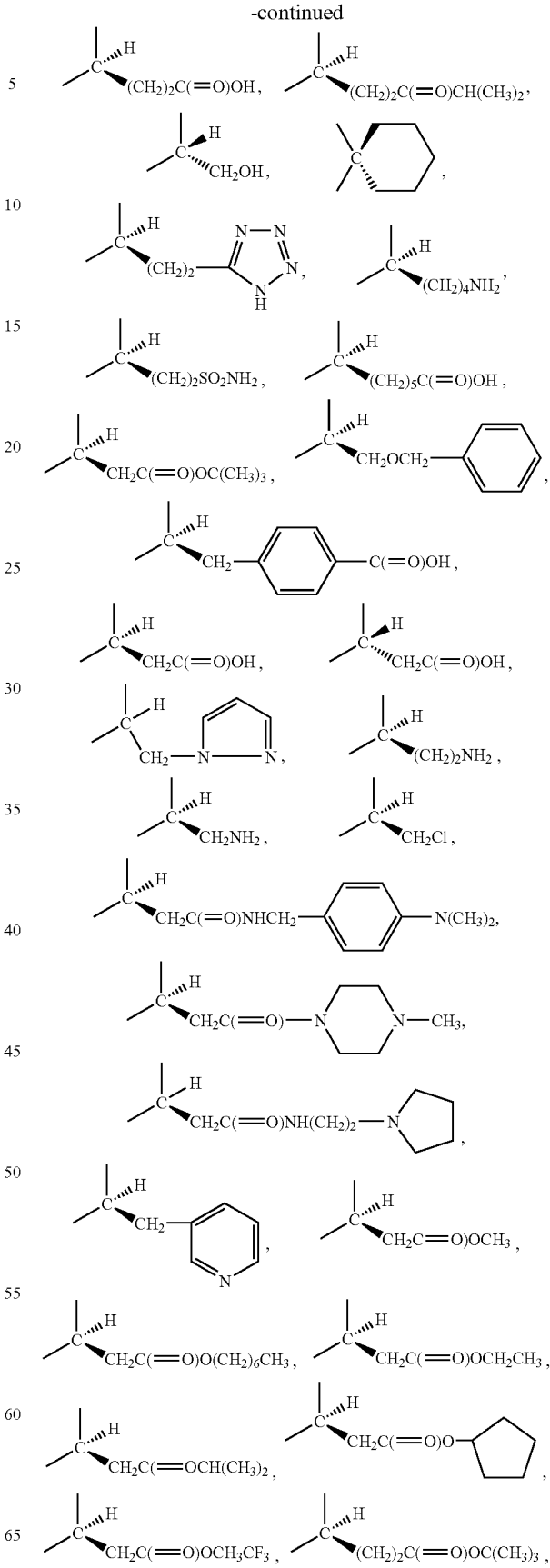

-continued

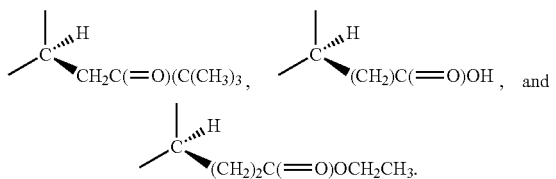

13. A pharmaceutical composition comprising a compound of claim 1, together with a pharmaceutically acceptable diluent or carrier.

14. A method of treating a male or female animal in the treatment of a condition selected from the group consisting of male erectile dysfunction, female arousal disorder, and hypertension comprising treating said animal with an effective amount of a pharmaceutical composition comprising a compound of claim 1, together with a pharmaceutically acceptable diluent or carrier.

15. The method of claim 14 wherein the condition is male erectile dysfunction.

16. The method of claim 15 wherein the treatment is an oral treatment.

17. The method of claim 14 wherein the condition is female arousal disorder.

18. The method of claim 17 wherein the treatment is an oral treatment.

19. A method of treating hypertension in a human or a nonhuman animal body, comprising administering to said body a therapeutically effective amount of acompound of claim 1, or a pharmaceutically acceptable salt or hydrate thereof.

20. The method of claim 19 wherein the hypertension is pulmonary hypertension or malignant hypertension.

21. A method for the treatment of male erectile dysfunction or female arousal disorder, comprising administration of an effective dose of a compound of claim 1, or a pharmaceutically acceptable salt or hydrate thereof, to an animal.

* * * * *

UNITED STATES PATENT AND TRADEMARK OFFICE
CERTIFICATE OF CORRECTION

PATENT NO.       : 7,034,027 B2
APPLICATION NO.  : 10/333146
DATED            : April 25, 2006
INVENTOR(S)      : Mark W. Orme et al.

It is certified that error appears in the above-identified patent and that said Letters Patent is hereby corrected as shown below:

Column 1, line 39, "haloC$_{1-6}$-alkyl," should be --haloC$_{1-6}$alkyl,--.

Column 1, line 40, "aryl C$_{1-3}$-alkyl," should be --arylC$_{1-3}$alkyl,--.

Column 1, line 67, "C$_{3-8}$-cycloalkyl," should be --C$_{3-8}$cycloalkyl,--.

Column 2, lines 2-3, "C$_{1-4}$alkyl-eneC(=O)NR$^a$,R$^b$," should be --C$_{1-4}$alkyleneC(=O)NR$^a$,R$^b$,--.

Column 2, line 7, "C(=O)-C$_{1-4}$alkyleneHet," should be --C(=O)C$_{1-4}$alkyleneHet,--.

Column 2, lines 24-25, "C$_{1-4}$alkyleneC(=O)C$_{1-4}$-alkyleneHet," should be --C$_{1-4}$alkyleneC(=O)C$_{1-4}$-alkyleneHet,--.

Column 2, line 27, "C(=O)-NR$^a$C$_{1-4}$alkyleneHet," should be --C(=O)-NR$^a$C$_{1-4}$alkyleneHet,--.

Column 2, lines 31-32, "haloC$_{1-6}$alkyl," should be --haloC$_{1-6}$alkyl,--.

Column 2, line 32, "arylC$_{1-3}$-alkyl," should be --arylC$_{1-3}$alkyl,--.

Column 2, line 33, "C$_{3-8}$-cycloalkyl," should be --C$_{3-8}$cycloalkyl,--.

Column 3, line 64, "C$_{1-4}$-alkyleneNR$^a$R$^b$," should be -- C$_{1-4}$alkyleneNR$^a$R$^b$,--.

Column 4, lines 12-13, "C$_{1-4}$alkyleneOC$_{1-3}$alkylenearyl," should be --C$_{1-4}$alkyleneOC$_{1-3}$alkylenearyl,--.

UNITED STATES PATENT AND TRADEMARK OFFICE
CERTIFICATE OF CORRECTION

PATENT NO.        : 7,034,027 B2
APPLICATION NO. : 10/333146
DATED             : April 25, 2006
INVENTOR(S)       : Mark W. Orme et al.

It is certified that error appears in the above-identified patent and that said Letters Patent is hereby corrected as shown below:

Column 5, lines 50-57,

" 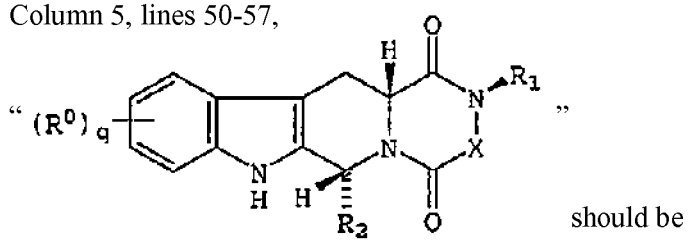 " should be

-- 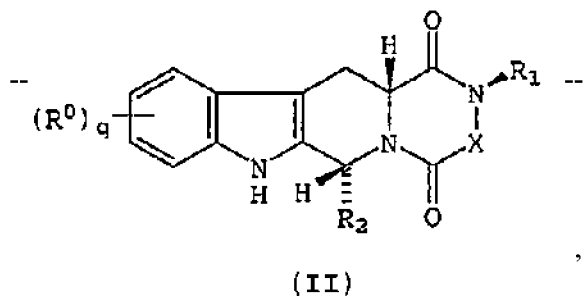 --,

Column 8, line 5, delete second structure.

Column 12, line 14, "NY, N.Y." should be --NY,NY--.

Column 12, line 32, "using a agent" should be --using an agent--.

Column 21, line 19, "$C_{24}H_{22}N_4O_5.H_2O$" should be --$C_{24}H_{22}N_4O_5 \cdot H_2O$--.

Column 21, line 24, "$C_6$" should be --C6--.

Column 22, line 60, "elutinq" should be --eluting--.

Column 23, line 4, "$C_{20}H_{16}N_4O_4.0.25$" should be --$C_{20}H_{16}N_4O_4 \cdot 0.25$--.

Column 24, line 7, "Carboline" should be --carboline--.

Column 24, line 19, "CDC1):" should be --$CDCl_3$):--.

Column 24, line 62, "$C_{23}H_{21}N_3O_4.0.4$" should be --$C_{23}H_{21}N_3O_4 \cdot 0.4$--.

Column 24, line 62, "5,35;" should be --5.35--.

UNITED STATES PATENT AND TRADEMARK OFFICE
CERTIFICATE OF CORRECTION

PATENT NO. : 7,034,027 B2 Page 3 of 7
APPLICATION NO. : 10/333146
DATED : April 25, 2006
INVENTOR(S) : Mark W. Orme et al.

It is certified that error appears in the above-identified patent and that said Letters Patent is hereby corrected as shown below:

Column 26, line 32, "136;5," should be --136.5,--.

Column 26, line 34, "55.4,.55.2," should be --55.4, 55.2--.

Column 26, line 43, "one-major" should be --one major--.

Column 27, line 39, "EXAMPLE 6" should be deleted.

Column 27, line 66, "$C_{21}H_{20}N_4O_3,0.75$" should be --$C_{21}H_{20}N_4O_3 \cdot 0.75$--.

Column 27, line 67, "N, 9, 13." should be --N, 9.13.--.

Column 30, line 41, "[1',2':1,;6]" should be--[1',2':1,6]--.

Column 30, line 66, "$C_{23}H_{19}N_3O_5,0.75$" should be --$C_{23}H_{19}N_3O_5 \cdot 0.75$--.

Column 33, Example 2, please add -- 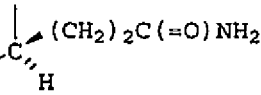 --

Column 39, line 1, "for $R^2$," should be --[1)] for $R^2$,--.

Column 39, line 39, "more-preferably" should be --more preferably--.

Column 39, line 61, "Marassas, Va.," should be --Manassas, Va.,--.

Column 39, line 64, "YEP-medium-containing" should be --YEP medium-containing--.

Column 40, line 27, "for,radioactivity should be --for radioactivity--.

Column 41, table 1, example 2, "2.2" should be --1.2--.

UNITED STATES PATENT AND TRADEMARK OFFICE
CERTIFICATE OF CORRECTION

PATENT NO. : 7,034,027 B2
APPLICATION NO. : 10/333146
DATED : April 25, 2006
INVENTOR(S) : Mark W. Orme et al.

It is certified that error appears in the above-identified patent and that said Letters Patent is hereby corrected as shown below:

Column 41, lines 58-66,

" 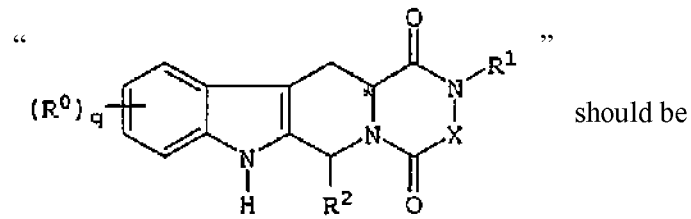  should be

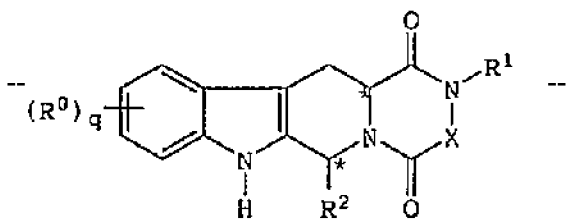  --

Column 42, lines 32-33, "$C_{1\text{-}4}alkyleneC(=O)C_{1\text{-}4}alkyleneHet$," should be --$C_{1\text{-}4}alkyleneC(=O)C_{1\text{-}4}alkyleneHet$,--.

Column 43, lines 6-7, "$C_{1\text{-}4}alkyleneC(=O)C_{1\text{-}4}alkyleneHet$;" should be --$C_{1\text{-}4}alkyleneC(=O)C_{1\text{-}4}alkyleneHet$;--.

Column 43, line 10, "$C^{1\text{-}4}alkyleneHet$," should be --$C_{1\text{-}4}alkyleneHet$,--.

Column 43, lines 10-11, "$haloC_1\text{-}6alkyl$," should be --$haloC_{1\text{-}6}alkyl$,--.

Column 43, lines 27-31,

" 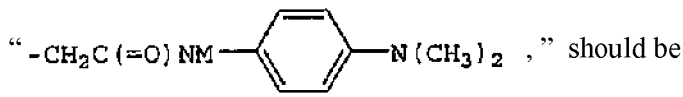 ," should be

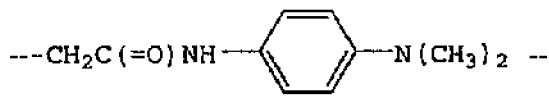 --

UNITED STATES PATENT AND TRADEMARK OFFICE
CERTIFICATE OF CORRECTION

PATENT NO.       : 7,034,027 B2
APPLICATION NO.  : 10/333146
DATED            : April 25, 2006
INVENTOR(S)      : Mark W. Orme et al.

It is certified that error appears in the above-identified patent and that said Letters Patent is hereby corrected as shown below:

Column 46, lines 1-14,

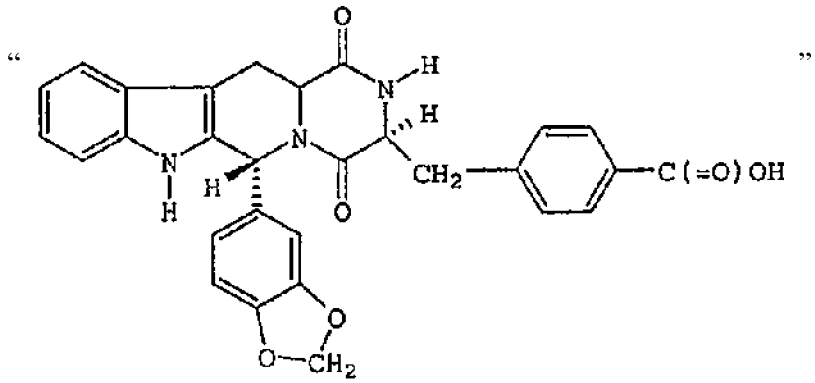

should be

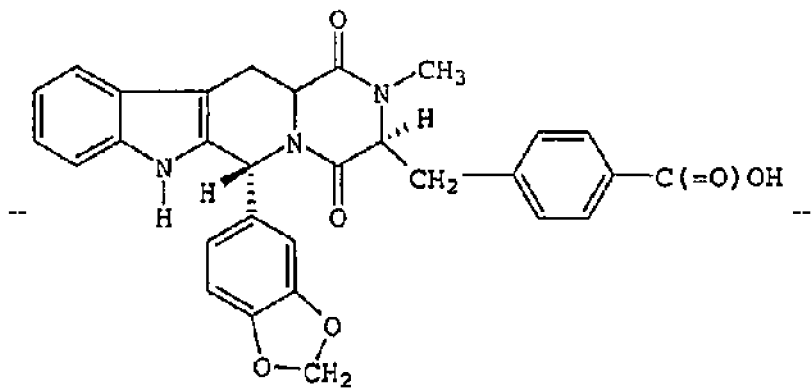

Column 46, line 65, "3S,6R,12aR)" should be --(3S,6R,12aR)--.

Column 46, line 66, "-ethyl]-1,2,3,6,7,12,12a-" should be -- -ethyl]-2,3,6,7,12,12a- --.

Column 47, first structure, lines 61-65,

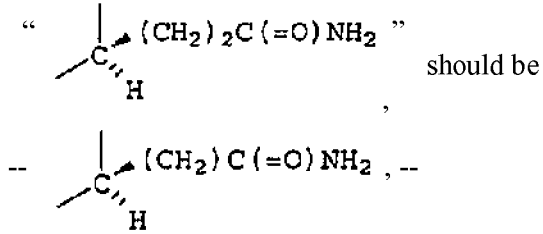

should be

UNITED STATES PATENT AND TRADEMARK OFFICE
CERTIFICATE OF CORRECTION

PATENT NO. : 7,034,027 B2
APPLICATION NO. : 10/333146
DATED : April 25, 2006
INVENTOR(S) : Mark W. Orme et al.

It is certified that error appears in the above-identified patent and that said Letters Patent is hereby corrected as shown below:

Column 48, first structure, lines 45-48,

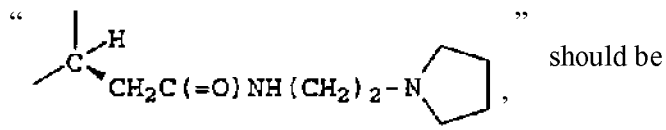   should be

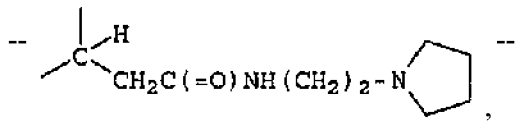

Column 48, second structure, lines 49-54,

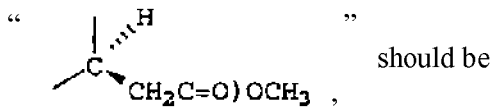   should be

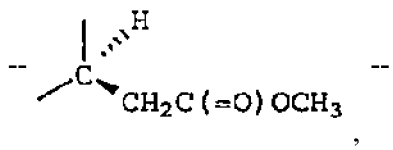

Column 48, first structure, line 59-62,

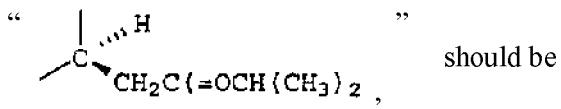   should be

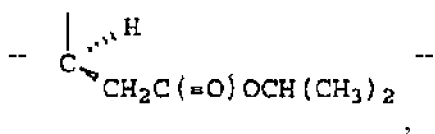

UNITED STATES PATENT AND TRADEMARK OFFICE
CERTIFICATE OF CORRECTION

PATENT NO. : 7,034,027 B2 Page 7 of 7
APPLICATION NO. : 10/333146
DATED : April 25, 2006
INVENTOR(S) : Mark W. Orme et al.

It is certified that error appears in the above-identified patent and that said Letters Patent is hereby corrected as shown below:

Column 49, second structure, lines 1-6,

"  " should be

-- 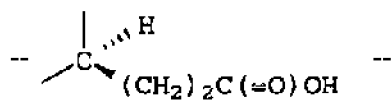 --

Column 50, line 11, "acompound" should be --a compound--.

Signed and Sealed this

Fifteenth Day of May, 2007

JON W. DUDAS
*Director of the United States Patent and Trademark Office*